United States Patent
Williams

(10) Patent No.: US 11,992,421 B2
(45) Date of Patent: May 28, 2024

(54) SYSTEM AND METHOD FOR SPINE FUSION USING AN EXPANDABLE CAGE

(71) Applicant: Seth K. Williams, Madison, WI (US)

(72) Inventor: Seth K. Williams, Madison, WI (US)

( * ) Notice: Subject to any disclaimer, the term of this patent is extended or adjusted under 35 U.S.C. 154(b) by 120 days.

(21) Appl. No.: 17/699,541

(22) Filed: Mar. 21, 2022

(65) Prior Publication Data

US 2022/0202589 A1 Jun. 30, 2022

Related U.S. Application Data

(63) Continuation of application No. 16/573,632, filed on Sep. 17, 2019, now Pat. No. 11,278,425, which is a continuation of application No. 15/431,292, filed on Feb. 13, 2017, now Pat. No. 10,426,631.

(60) Provisional application No. 62/297,852, filed on Feb. 20, 2016.

(51) Int. Cl.
*A61F 2/44* (2006.01)
*A61F 2/46* (2006.01)
*A61B 17/02* (2006.01)
*A61F 2/30* (2006.01)

(52) U.S. Cl.
CPC ............ *A61F 2/447* (2013.01); *A61F 2/4611* (2013.01); *A61B 2017/0256* (2013.01); *A61F 2002/30383* (2013.01); *A61F 2002/30515* (2013.01); *A61F 2002/30556* (2013.01); *A61F 2002/30593* (2013.01); *A61F 2002/30616* (2013.01); *A61F 2002/30772* (2013.01); *A61F 2002/4622* (2013.01); *A61F 2002/4629* (2013.01)

(58) Field of Classification Search
CPC ...... A61F 2/4425; A61F 2/447; A61F 2/4611; A61F 2002/443; A61F 2002/4475; A61F 2002/4615; A61F 2002/4622; A61F 2002/4629
See application file for complete search history.

(56) References Cited

U.S. PATENT DOCUMENTS

| | | | | |
|---|---|---|---|---|
| 6,562,074 B2* | 5/2003 | Gerbec | ................ | A61F 2/4611 623/17.15 |
| 7,118,580 B1* | 10/2006 | Beyersdorff | .......... | A61F 2/4425 623/17.15 |
| 8,715,351 B1* | 5/2014 | Pinto | ....................... | A61F 2/447 623/17.13 |
| 8,828,019 B1* | 9/2014 | Raymond | ............... | A61F 2/442 606/105 |
| 9,114,026 B1* | 8/2015 | McLean | ................. | A61F 2/4455 |
| 10,045,861 B2* | 8/2018 | McLean | ................ | A61F 2/4611 |
| 10,426,631 B2* | 10/2019 | Williams | ................ | A61F 2/447 |
| 11,278,425 B2* | 3/2022 | Williams | .............. | A61F 2/4611 |

(Continued)

*Primary Examiner* — Eric S Gibson
(74) *Attorney, Agent, or Firm* — Foley & Lardner LLP

(57) ABSTRACT

An expandable cage system for use in spinal surgery includes a top portion having an outwardly extending top arm, and a bottom portion having an outwardly extending bottom arm. The bottom arm is configured to engage with the top arm such that upon engagement, the top portion and the bottom portion are substantially restricted from movement relative to each other in an anterior-posterior direction, and in a medial-lateral direction. The expandable cage system further includes a removable shim configured to be positioned between the top portion and the bottom portion to hold the expandable cage in an expanded position within a spinal cavity.

19 Claims, 25 Drawing Sheets

(56) References Cited

U.S. PATENT DOCUMENTS

| | | | |
|---|---|---|---|
| 2008/0021559 A1* | 1/2008 | Thramann | A61F 2/447 623/17.16 |
| 2008/0300598 A1* | 12/2008 | Barreiro | A61F 2/442 606/90 |
| 2012/0191190 A1* | 7/2012 | Trieu | A61F 2/442 623/17.11 |
| 2013/0090735 A1* | 4/2013 | Mermuys | A61F 2/442 623/17.16 |
| 2017/0239062 A1* | 8/2017 | Williams | A61F 2/4611 |
| 2020/0008954 A1* | 1/2020 | Williams | A61F 2/447 |
| 2022/0202589 A1* | 6/2022 | Williams | A61F 2/4611 |

* cited by examiner

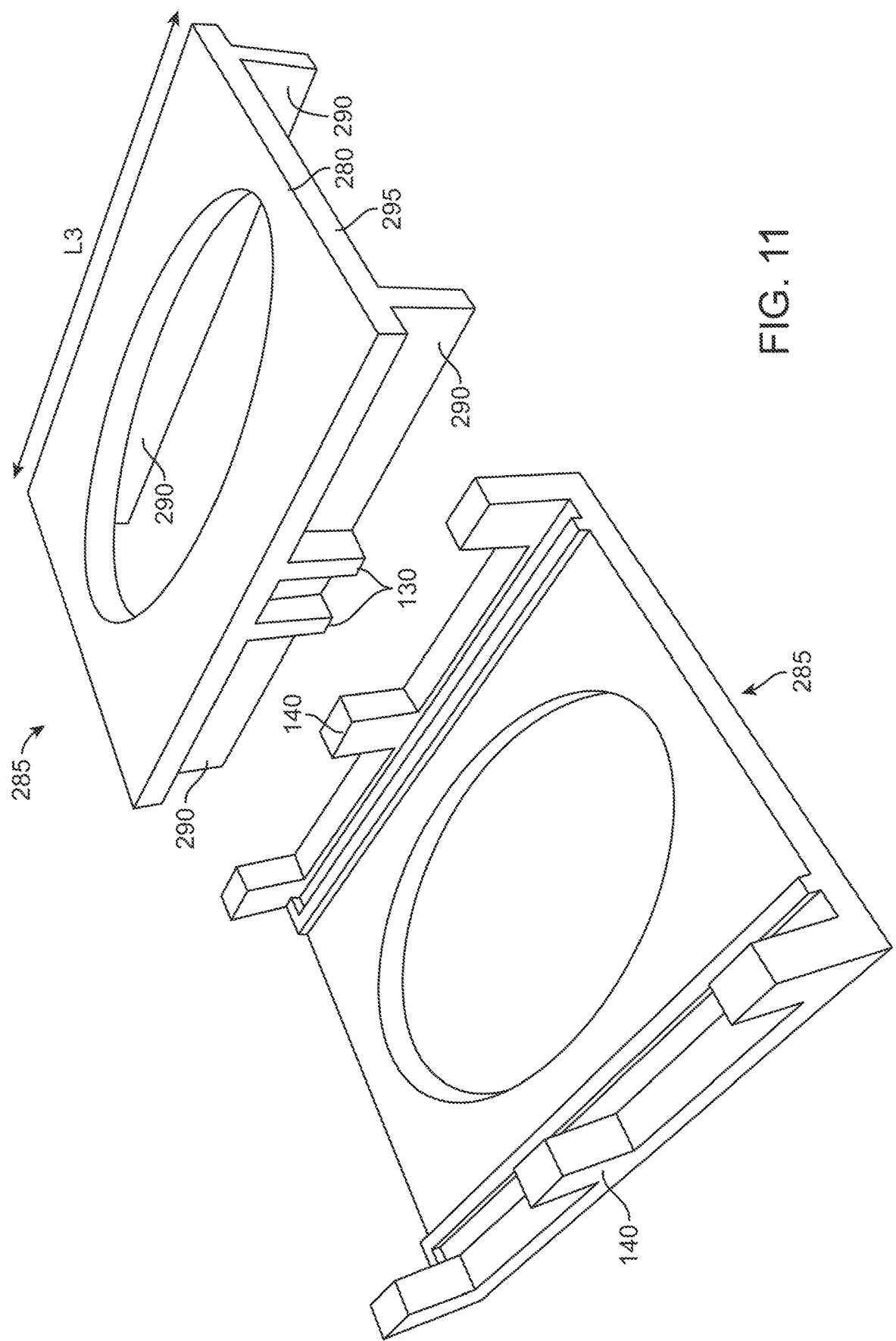

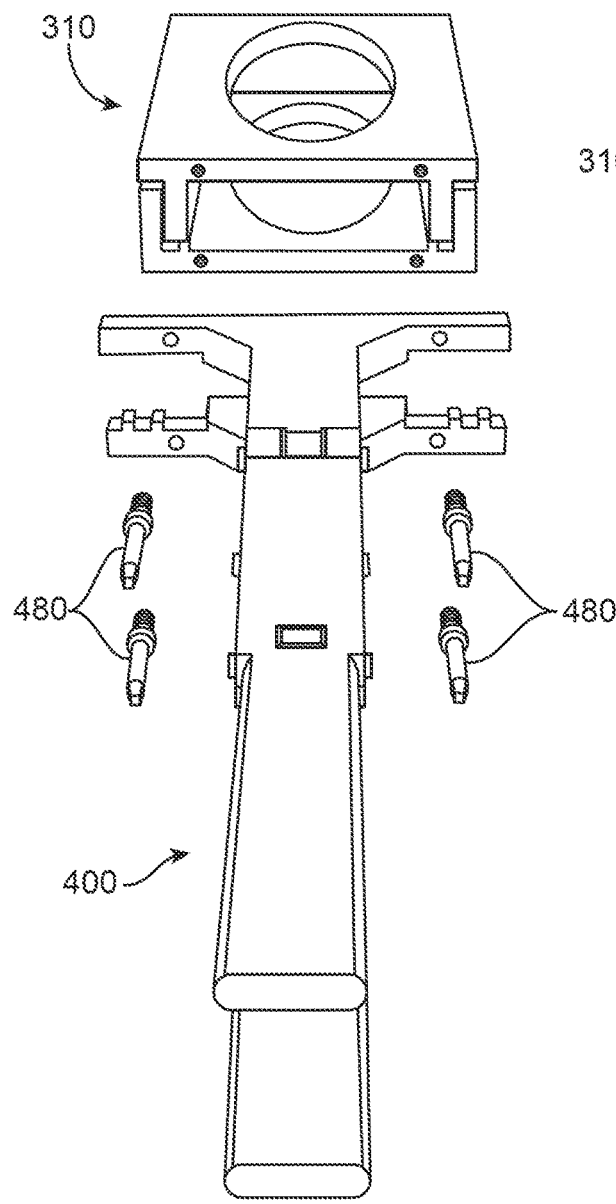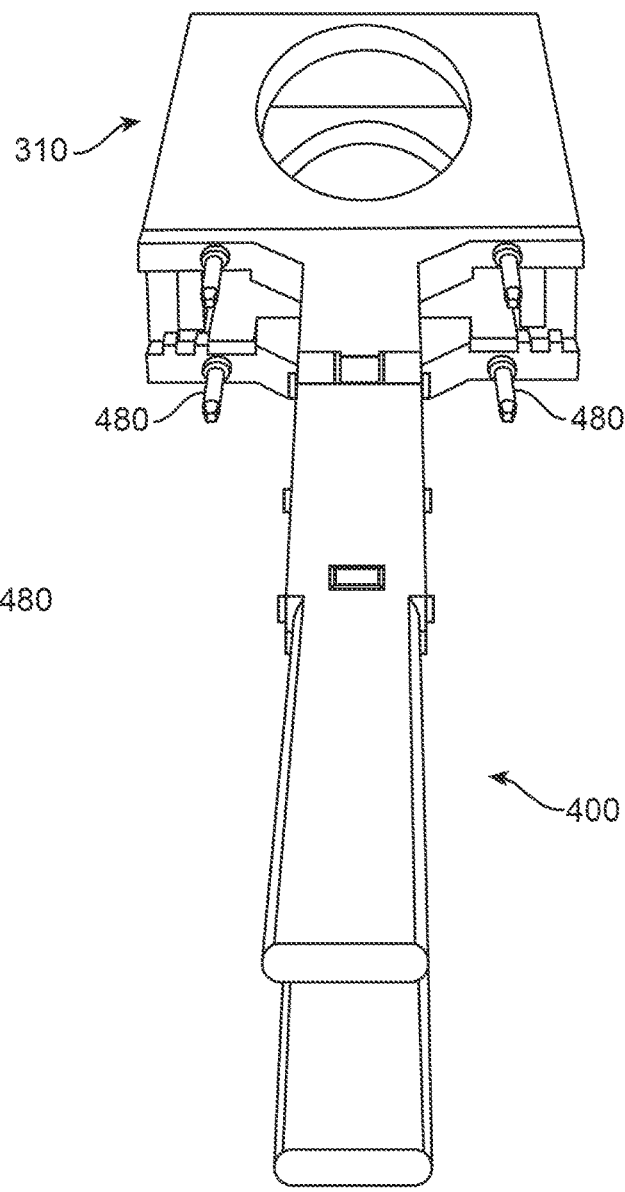
FIG. 14E
FIG. 14F

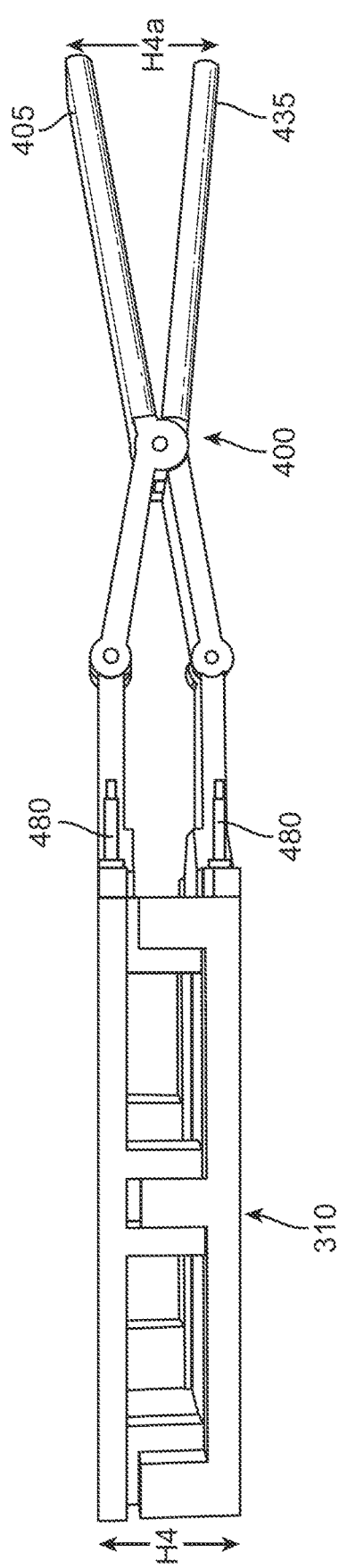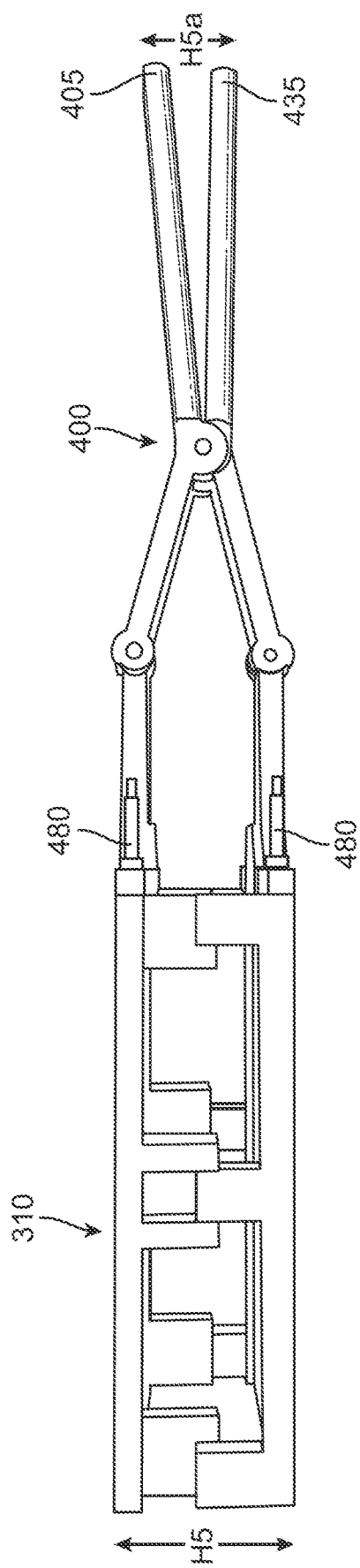
FIG. 14G
FIG. 14H

SYSTEM AND METHOD FOR SPINE FUSION USING AN EXPANDABLE CAGE

CROSS-REFERENCE TO RELATED APPLICATIONS

The present application is a continuation of U.S. patent application Ser. No. 16/573,632 filed on Sep. 17, 2019, which is a continuation of U.S. patent application Ser. No. 15/431,292 filed on Feb. 13, 2017, which claims priority to U.S. Provisional Patent App. No. 62/297,852 filed on Feb. 20, 2016, the entireties of which are incorporated by reference herein.

BACKGROUND

The following description is provided to assist the understanding of the reader. None of the information provided or references cited is admitted to be prior art.

The lumbar spine refers to the lower back, and is where a human's spinal column curves inward toward the abdomen. The lumbar spine, which typically starts five to six inches below the shoulder blades, connects with the thoracic spine at the top and the sacral spine at the bottom. A human lumbar spine typically includes five vertebrae, although some individuals have four or six vertebrae in their lumbar spine. There are several different conditions that can affect the lumbar spine and cause pain, including disk problems, scoliosis and other spinal deformities, spondylolisthesis, stenosis, tumors, and fractures. These conditions may result from trauma, disease, and degenerative conditions caused by aging, injury, or may be idiopathic. Non-operative treatments such as physical therapy, medications, exercise, and/or injections may or may not relieve the symptoms associated with these disorders. Surgery may be used to help alleviate pain in some individuals who are suffering from disk problems and other ailments. Surgery may include decompression of the neural elements, correction of deformity, removal of disk material, instrumentation, and/or implantation of prosthetic devices.

SUMMARY

In accordance with at least some aspects of the present disclosure, an expandable cage system for use in spinal surgery is disclosed. The expandable cage system includes a top portion having an outwardly extending top arm, and a bottom portion having an outwardly extending bottom arm. The bottom arm is configured to engage with the top arm such that upon engagement, the top portion and the bottom portion are substantially restricted from movement relative to each other in an anterior-posterior direction, and in a medial-lateral direction. The expandable cage system further includes a removable shim configured to be positioned between the top portion and the bottom portion to hold the expandable cage in an expanded position within a spinal cavity.

In accordance with at least some other aspects of the present disclosure, a method is disclosed. The method includes inserting an expandable cage within a spinal cavity, and expanding the expandable cage to an expanded position within the spinal cavity. The expanding includes moving a top portion of the expandable cage away from a bottom portion of the expandable cage using an expansion device. The method further includes inserting a first shim and a second shim within the expandable cage and between the top portion and the bottom portion for holding the expandable cage in the expanded position. The method additionally includes removing the expansion device.

In accordance with yet other aspects of the present disclosure, another method is disclosed. The method includes inserting an expandable cage in a contracted position within a spinal cavity, such that the expandable cage includes a top portion engaged with a bottom portion. The method also includes positioning the expandable cage between a first vertebra and a second vertebra, expanding the top portion relative to the bottom portion for obtaining an expanded position for facilitating fusion of the first vertebra and the second vertebra, and inserting a shim between the top portion and the bottom portion for holding the expandable cage in the expanded position.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 11 is a perspective view depicting the top portion and the bottom portion of the expandable cage, in accordance with yet another illustrative embodiment.

FIG. 14E is a top perspective view depicting the expandable cage and the insertion and expansion device and the fasteners in an assembly position, in accordance with an illustrative embodiment.

FIG. 14F is a top perspective view depicting the expandable cage and the insertion and expansion device and the fasteners in an assembled position, with fasteners securing the expandable cage to the insertion and expansion device, in accordance with an illustrative embodiment.

FIG. 14G is a side perspective view depicting the expandable cage and the insertion and expansion device and the fasteners in an assembled position, with fasteners securing the expandable cage to the insertion and expansion device, in accordance with an illustrative embodiment. The cage is depicted in a collapsed or contracted configuration.

FIG. 14H is a side perspective view depicting the expandable cage and the insertion and expansion device and the fasteners in an assembled position, with fasteners securing the expandable cage to the insertion and expansion device, in accordance with an illustrative embodiment. The cage is depicted in an expanded configuration.

Figure 1A:
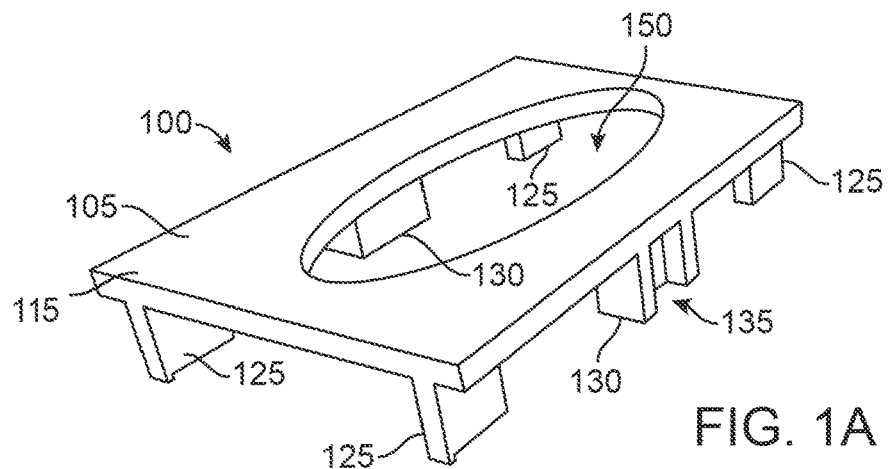
FIG. 1A is a perspective view depicting a top surface of a top portion of a lateral extrinsically expandable cage, in accordance with an illustrative embodiment.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

A lateral, or alternatively anterolateral lumbar spine fusion (collectively referred to as "spine fusion" herein) is typically performed through one or more incisions placed on a lateral or anterolateral portion of a human abdomen. The incision(s) are just large enough to accommodate a retractor device that allows visualization of the human spine. The spine is typically approached through a retroperitoneal space in the abdominal cavity. Upon exposing the spinal disk to be fused, a diskectomy or other surgical treatments may be performed through standard techniques well known to those of skill in the art. As part of the diskectomy or the other surgical treatments, intervertebral or structural cages may be inserted into a disk space or spinal cavity of the spine to correct spinal deformity, to stabilize the spine, and/or to deliver biological material to promote a bony fusion between two vertebral bodies of the spine.

Specifically, once the diskectomy is performed, vertebral endplates are prepared for the bony fusion, and a structural bone graft or a structural cage containing a bone growth promoting substance such as a bone graft is placed into the intervertebral space. The structural cage typically provides structural support between the vertebral bodies that are to be fused. The structural cage may be optionally held in place with a variety of techniques, including an interference screw, screws that are integrated into a plate, or with a plate that may be attached to or be separate from the structural cage.

The structural cage that is placed in the intervertebral space may be static or dynamic. A static cage has fixed dimensions that are determined upon manufacture of the static cage. In contrast, an expandable cage is dynamic and may be inserted into the intervertebral space prior to expansion, and then expanded once the expandable cage is in position. Some of the benefits of an expandable cage compared to a static cage are ease of insertion because the expandable cage may be inserted in a lowest height profile (or in other words, in a maximally contracted position) of the expandable cage, and then expanded to the desired height after insertion, thereby reducing trauma to the vertebral endplates during insertion. Additionally, an expandable cage has the ability to expand to a taller overall cage height because cage insertion is less traumatic to the vertebral endplates. A drawback of an expandable cage compared to a static cage is the mechanism by which the cage is expanded. Conventionally, the expandable cage is expanded intrinsically and the intrinsic mechanism used to expand the expandable cage becomes a permanent part of the expandable cage. Therefore, the intrinsic mechanism occupies space within the expandable cage and decreases the amount of the bone growth promoting substance (e.g., bone graft) that may be placed within the expandable cage.

Additionally, the intrinsic mechanism used to expand the expandable cage after insertion adds technical complexity to the overall process. The intrinsic mechanism also increases the overall cost of the expandable cage, and potentially becomes a site of mechanical weakness. The present disclosure overcomes at least some of these disadvantages by providing a surgical system that combines the benefits of an expandable cage with the simplicity of a static cage. Specifically, the surgical system of the present disclosure provides a spinal construct including a lateral extrinsically expandable cage, and components related to the expandable cage, and its surgical implantation. The expandable cage may be expanded using an extrinsic mechanism upon implantation in the intervertebral disk space or spinal cavity.

In particular, the expandable cage of the present disclosure includes four primary components—a top portion, a bottom portion, a first shim, and a second shim. The top portion and the bottom portion of the cage are configured to mate or engage together in a manner that restricts movement of the top portion with respect to the bottom portion in anterior-posterior (e.g., front-back) and medial-lateral (e.g., lefts side-right side) directions. The expandable cage is further configured to be expanded in a cephalad-caudal (e.g., vertical or top-bottom) direction, thereby making the expandable cage taller after installation.

The expandable cage may be expanded extrinsically using an extrinsic (e.g., outside the spinal cavity) removable insertion and expansion device configured to hold the expandable cage in an assembled and expanded state while the first shim and the second shim are inserted. Specifically, the insertion and expansion device is configured to attach to the expandable cage, and facilitate insertion and positioning of the expandable cage within the spinal cavity. After insertion, the insertion and expansion device temporarily holds the top portion relative to the bottom portion in an expanded position to facilitate insertion of the shims. The first shim and the second shim are then inserted within the expandable cage to hold the expandable cage in the expanded form. The insertion and expansion device is removed upon inserting the first shim and second shim within the expandable cage. Shims of different heights may be utilized to control the overall height and shape of the expandable cage.

By virtue of using the surgical system of the present disclosure, the expandable cage may be used to treat spinal conditions such as, for example, stenosis, spondylolisthesis, scoliosis, kyphosis, other deformities, trauma, tumor, infection, disk herniation, and degenerative disk disease. The expandable cage may also be used for fusion in the thoracic or lumbar spine, and across the thoracolumbar and lumbosacral junctions. The expandable cage may additionally be employed for surgical treatments in a patient in a lateral, supine, oblique, or prone position, and may employ various approaches to the spine, including anterior, anterolateral, and lateral. The expandable cage may be used, in addition to humans, on animals, bone models, and other non-viable substrates, for example, for use in testing, demonstration, and training.

Figure 1B:
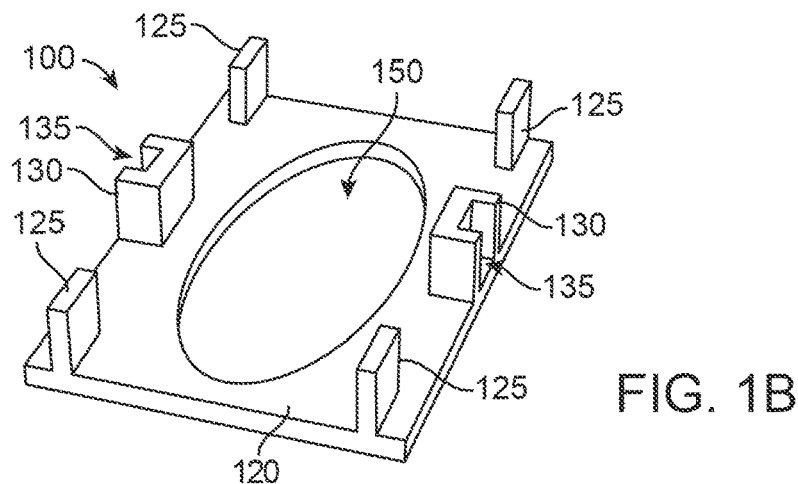
FIG. 1B is a perspective view depicting a bottom surface of the top portion of the expandable cage, in accordance with an illustrative embodiment.
Figure 1C:
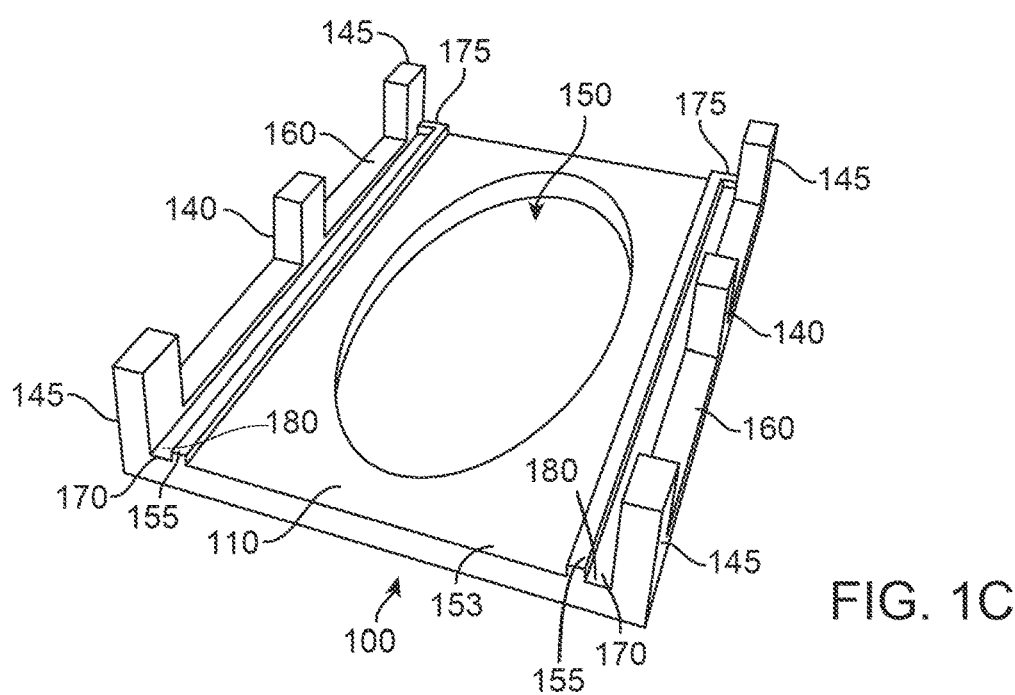
FIG. 1C is a perspective view of a bottom portion of the expandable cage, in accordance with an illustrative embodiment.

Referring now to FIGS. 1A-1C, perspective views depicting an expandable cage 100 are shown, in accordance with illustrative embodiments. The expandable cage 100 includes a top portion 105 (see FIGS. 1A-1B) and a bottom portion 110 (see FIG. 1C). The top portion 105 is also referred to herein as top part, upper part/portion, and superior part/portion, and the bottom portion 110 is also referred to herein as bottom part, lower part/portion, and inferior part/portion.

With specific reference to FIGS. 1A and 1B, the top portion 105 of the expandable cage 100 includes a top surface 115 (also referred to herein as uppermost surface) and a bottom surface 120 (also referred to herein as undersurface). The top surface 115 of the top portion 105 is configured to engage an inferior endplate of an upper vertebral body in a spinal fusion surgical procedure, while the bottom surface 120 of the top portion is configured to align the expandable cage 100 in an upside down position after surgical implantation. Although the top portion 105 and the bottom portion 110 have been shown as being generally rectangular in shape, in other embodiments, the top portion and the bottom portion may assume other shapes and sizes. In some embodiments, the expandable cage 100 may be approximately forty to sixty millimeters (40-60 mm) in medial-to-lateral length, fifteen to twenty five millimeters (15-25 mm) in anterior-posterior width, and six to thirty millimeters (6-30 mm) in superior-to-inferior height. In other embodiments, one or more of the dimensions of the expandable cage 100 may vary depending upon the patient anatomy in which the expandable cage is used.

The top portion 105 includes arms 125 and 130 (also referred to herein as posts or top arms) that project outwardly from the bottom surface 120 of the top portion. In some embodiments, the arms 125 are provided at or adjacent to the four corners of the top portion 105. Furthermore, in some embodiments, the arms 125 are configured as single outward projections. Also, in some embodiments, the arms 130 are provided equidistant (or substantially equidistant) between the arms 125, and are configured with three outward projections aligned at ninety degrees to each other, thereby creating a slot 135. The slot 135 is configured to receive and mate (e.g., engage) with corresponding arms 140 (see FIG. 1C) extending outwardly from the bottom portion 110. By virtue of receiving the arms 140, the arms 130 confine the movement of the arms 140, thereby facilitating assembly or engagement of the top portion 105 to the bottom portion 110, and restricting movement of the expandable cage 100 in the anterior-posterior and medial-lateral directions. Notwithstanding that four of the arms 125 and two of the arms 130 are shown in FIGS. 1A and 1B, in other embodiments, greater than or fewer than four arms for the arms 125, and greater than or fewer than two arms for the arms 130, may be provided in the top portion 105. Additionally, the shape, size, orientation, and other configuration of the arms 125 and the arms 130 may vary in other embodiments.

The directions anterior-posterior, and medial-lateral are well understood terms to people of skill in the art. For example, an anterior-posterior direction may refer to a horizontal, substantially horizontal, front-back, or back-front direction (e.g., rib-spine or spine-rib direction of a human body), while a medial-lateral direction may refer to a horizontal, substantially horizontal, left-right, or right-left direction (e.g., left hand-right hand or right hand-left hand direction of a human body). Similarly, a cephalad-caudal direction or a superior-inferior direction may refer to a vertical, substantially vertical, top-bottom, or bottom-top direction (e.g., head-toe or toe-head direction of the human body). Generally speaking, as used herein, the anterior-posterior and medial-lateral directions refer to motion that offsets the top portion 105 relative to the bottom portion 110 (e.g., at an angle) without impacting (or substantially impacting) the distance or height between the top portion and the bottom portion. Likewise, the cephalad-caudal direction or superior-inferior directions refer to motion that varies the distance (e.g., height) between the top portion 105 and the bottom portion 110 without offsetting (or substantially offsetting) the angle of the top portion relative to the bottom portion.

Referring now to FIG. 1C in conjunction with FIGS. 1A and 1B, the bottom portion 110 additionally includes arms 145 that project outwardly from a bottom surface 153 of the bottom portion. The arms 145 are situated at or adjacent to the four corners of the bottom portion 110, and are configured to engage (e.g., abut) the arms 125 upon assembly or engagement. In some embodiments and as shown, the arms 140 and the arms 145 are similar in configuration, or in alternative embodiments, those arms may be configured differently from each other. Additionally, similar to the arms 125 and the arms 130, the arms 140 and the arms 145 may vary in shape, size, orientation, and configuration from one embodiment to another, so long as the arms 125 are configured to mate (e.g., engage) with the arms 145, and the arms 140 are configured to mate (e.g., engage) with the arms 130.

The top portion 105 and the bottom portion 110 of the expandable cage 100 also include an opening 150, in some embodiments, to allow a bone graft promoting material (e.g., bone graft) to be placed within that opening. By placing the bone graft promoting material within the opening 150, the expandable cage 100 allows the bone graft promoting material to come into contact with adjacent vertebral endplates to facilitate fusion thereof. The shape, size, and configuration of the opening 150 may vary in other embodiments from that shown. In some embodiments, the shape, size, and configuration of the opening 150 on the top portion 105 may vary from the shape, size, and configuration of the opening on the bottom portion 110. In yet other embodiments, the opening 150 may be absent altogether.

In alternative embodiments, the arms 125, 130, 140, and 145 may be configured to articulate via a hinge or similar rotatory component with respect to the top portion 105 and the bottom portion 110. In this manner, shims (see FIG. 4) of different heights anteriorly and posteriorly may be placed, resulting in a cage (e.g., the expandable cage 100) with a taller height anteriorly than posteriorly, or a taller height posteriorly than anteriorly, which may result in the cage assuming a lordotic or kyphotic configuration, thereby enabling a surgeon to control, to some degree, a patient's sagittal alignment during a surgical treatment.

Furthermore, the bottom portion 110 includes, in some embodiments, outward projections 155 and 160 to create grooves 170. In some embodiments, the grooves 170 may be bound on one end by end projections 175 that connect the outward projections 155 and 160. In some embodiments, the expandable cage 100 may be positioned during insertion such that openings 180 (e.g., the end of the grooves 170 that is opposite to the end projections 175) face the lateral surgical incision to accommodate a shim (See FIG. 4) within the grooves, and the end projections are facing opposite to the lateral incision. The end projections 175 prevent the shim from being over-inserted (e.g., from extending beyond the profile of the expandable cage 100). In alternative embodiments, the grooves 170 may be surrounded by walls on all four sides by the presence of an additional end projection instead of the openings 180. Furthermore, in some embodiments, corresponding grooves may be provided on the top portion in addition to, or instead of, the grooves 170 on the bottom portion 110. Additionally, in some embodiments, each of the grooves 170 may be of varying widths. In some embodiments, the grooves 170 may be configured based upon the configuration of the shims that those groves are designed to receive. A top surface (e.g., the surface opposite the bottom surface 153) of the bottom portion 110 is configured to engage a superior endplate of the lower vertebral body in a spinal fusion.

Figure 2:
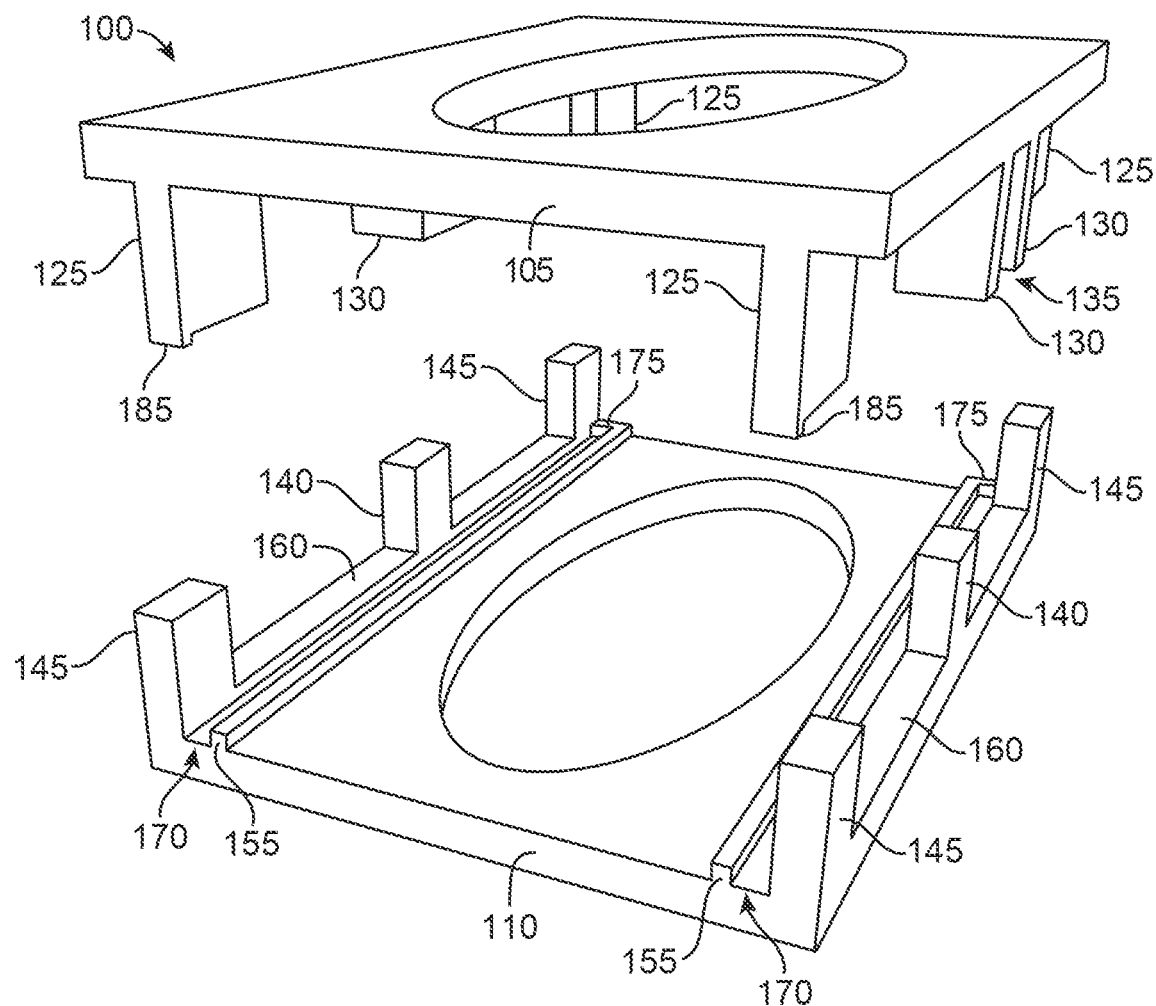
FIG. 2 is a perspective view depicting the top portion and the bottom portion of the expandable cage in an assembling position, in accordance with an illustrative embodiment.

Turning now to FIG. 2, a perspective view depicting the top portion 105 and the bottom portion 110 of the expandable cage 100 in an assembling position is shown, in accordance with illustrative embodiments. As discussed above, the arms 125 and the arms 130 project outwardly from the top portion 105, and are configured to mate (e.g., engage) with the arms 145 and 140, respectively, of the bottom portion 110. Specifically, in some embodiments, the arms 125 of the top portion 105 are configured such that upon engaging the arms 145 of the bottom portion 110, the arms 125 rest upon the outward projections 155 in a maximally contracted position (e.g., when the top portion is engaged with the bottom portion, but before inserting of shims, discussed below). Similarly, the arms 130 of the top portion 105 are configured such that upon engaging the arms 140 of the bottom portion 110, the arms 140 fit within the slot 135 of the arms 130. For example, in some embodiments, the arms 145 may be configured to slide within the slot 135, in a relationship explained further below in FIG. 3.

Furthermore, in some embodiments, at least some of the arms 125 include a lip 185 to prevent a shim (See FIG. 4) from migrating after insertion into the grooves 170. In some embodiments, the lip 185 may be provided on those ones of the arms 125 that upon engagement with the arms 145 correspond to the openings 180 (e.g., opposite the end projections 175). Thus, the lip 185, along with the end projections 175, prevents the shim from sliding out of the grooves 170 after being inserted, or in other words, restricts motion of the shim within the grooves. In other embodiments, the lip 185 may be absent. For example, in those embodiments where the openings 180 are provided with end projections similar to the end projections 175, the lip 185 may not be needed. In yet other embodiments, all of the arms may be configured with the lip 185, and the end projections 175 may not be needed.

Furthermore, as discussed above, in some embodiments, the outward projections 155 and 160 from the bottom surface 153 of the bottom portion 110 create the grooves 170 that are configured to accommodate shims, shown and discussed below in FIG. 4. In some embodiments, the expandable cage 100 may be positioned during insertion into the spinal cavity such that the grooves 170 may be open (e.g., via the openings 180) on the side of the expandable cage 100 facing the lateral surgical incision, and the end projections 175 may be located on the side of the expandable cage 100 opposite the lateral incision and prevent the shim from being over-inserted (e.g., sliding out of the grooves 170). In alternative embodiments, the grooves 170 may be surrounded by walls on all four sides by the presence of an additional outward projection from the bottom surface 153 of the bottom portion 110 of the expandable cage 100, located on the side of the expandable cage facing the lateral surgical incision (e.g., in the openings 180).

Figure 3:
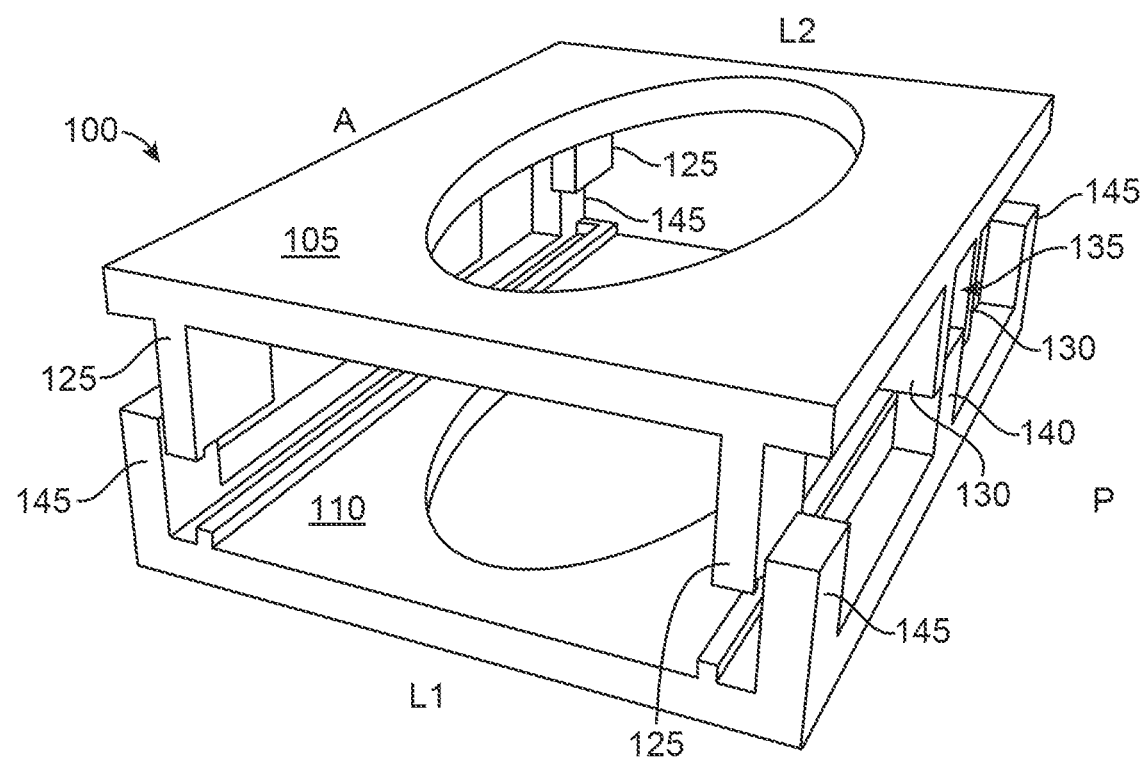
FIG. 3 is a perspective view depicting the top portion and the bottom portion of the expandable cage in another assembling position, in accordance with an illustrative embodiment.

Referring now to FIG. 3, a perspective view depicting the top portion 105 and the bottom portion 110 of the expandable cage 100 in another assembling position is shown, in accordance with illustrative embodiments. Specifically, in some embodiments, when the top portion 105 is engaged or mated with the bottom portion 110 via the arms 125, 130, 140, and 145, the arms 130 form the slot 135 that receives the arms 140, thus restraining movement of the top portion with respect to the bottom portion in the anterior-posterior and medial-lateral directions, allowing only cephalad-caudal expansion or contraction of the top portion with respect to the bottom portion. Specifically, when the top portion 105 is engaged or mated with the bottom portion 110, the arms 125 are adjacent to (e.g., abut) the arms 145, further restraining movement of the top portion with respect to the bottom portion in the anterior-posterior direction, but allowing cephalad-caudal expansion or contraction of the top portion with respect to the bottom portion.

Additionally, when the expandable cage 100 is inserted into the intervertebral disk space or spinal cavity during an operation, the side marked "A" on FIG. 3 faces anteriorly, the side marked "P" faces posteriorly, the side marked "L1" faces the lateral side of the patient towards the incision, and the side marked "L2" faces the lateral side of the patient opposite the side of the incision.

Figure 4:
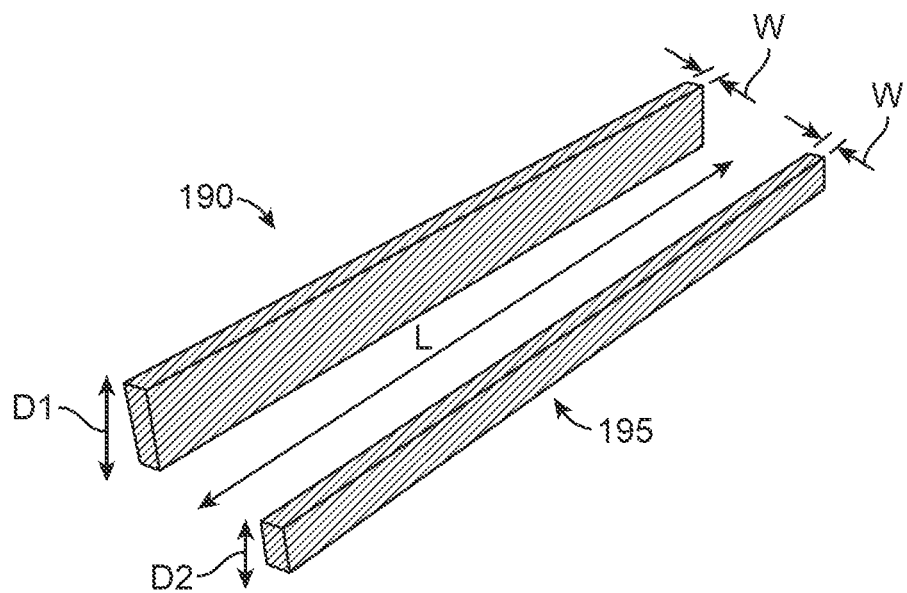
FIG. 4 is a perspective view depicting shims that hold the expandable cage in an expanded position, in accordance with an illustrative embodiment.

Turning now to FIG. 4, example shims 190 and 195 are shown, in accordance with illustrative embodiments. In some embodiments, the shims 190 and 195 are rectangular in shape and have same (or similar) length, L, and same (or similar) width, W, but vary in height, D1 and D2. Generally speaking, the length, L, of the shim 190 and the shim 195 corresponds substantially to the length of the bottom portion 110 and, particularly, to the length of the grooves 170 of the bottom portion. Likewise, the width, W, of the shim 190 and the shim 195 may vary based upon the width of the grooves 170.

With respect to the height, D1, of the shim 190, and the height, D2, of the shim 195, by varying the height of those shims, the height of the expandable cage 100 may be varied upon expansion. In some embodiments, two of the shims (e.g., two of the shim 190 or two of the shim 195) may be used to expand the expandable cage 100 to an expanded position. In other embodiments, greater than or fewer than two of the shims may be used. Further, the location of the shims (e.g., the shim 190 and the shim 195) and, therefore, the location of the grooves 170 on the bottom portion 110 of the expandable cage 100 may vary in other embodiments. Additionally, in some embodiments, each of the two shims that is used for expanding the expandable cage 100 have the same or similar height. In other embodiments, it may be desirable to have those shims be of varying heights. Thus, the configuration of the shims (e.g., the shim 190 and the shim 195), the number of shims used, and the location of the shims within the expandable cage 100 may vary from one embodiment to another.

As an example, the height, D1, of the shim 190 is shown taller than the height, D2, of the shim 195. Thus, by replacing the shim 190 with the shim 195, or vice-versa, the height of the expandable cage 100 may be adjusted for adjusting the final cage configuration and height.

Figure 5A:
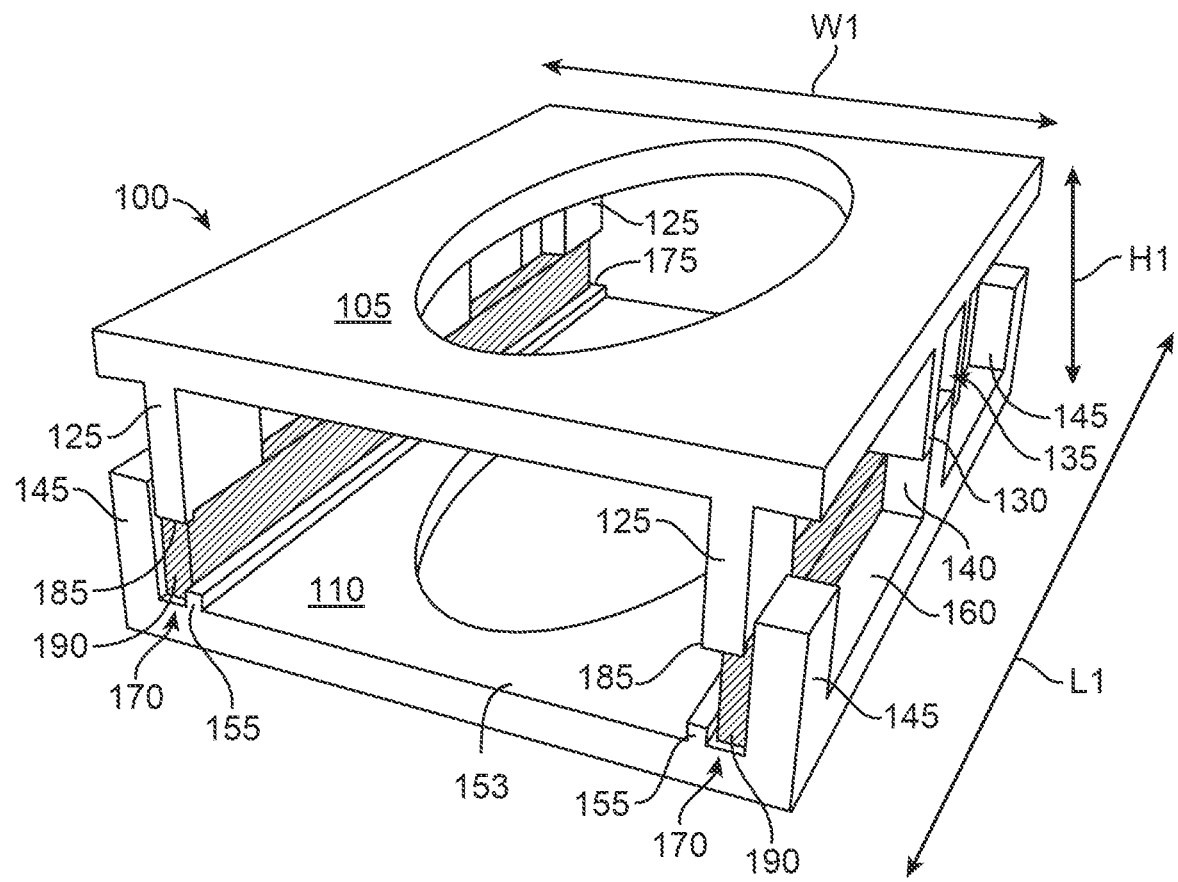
FIG. 5A is a perspective view depicting the top portion and the bottom portion of the expandable cage in an engaged position, with the shims inserted to expand the expandable cage to a first height, in accordance with an illustrative embodiment.

Referring now to FIG. 5A, a perspective view depicting the expandable cage 100 in a final, fully engaged and expanded form after surgical implantation in a patient is shown, in accordance with illustrative embodiments. An instance of the shim 190 is inserted into each of the grooves 170 that are formed by the outward projections 155 and 160, as well as the end projections 175. In some embodiments, an instance of the shim 190 is inserted into each of the grooves 170 after the insertion of the expandable cage 100 into the spinal cavity. In other embodiments, the shims 190 may be inserted into the expandable cage 100 before inserting the expandable cage into the spinal cavity. After the insertion of the shim 190 into the grooves 170, the lip 185 of the arms 125 of the top portion 105 engages with the shim on the side of the openings 180, and combined with the end projections 175 on the opposite lateral side of the grooves, constrain the shim and prevent migration of the shim in lateral directions. Additionally, in some embodiments, after insertion of the shim 190, a bottom surface (e.g., inferior-most surface) of the arms 125 rests upon a top surface (e.g., superior-most surface) of the shim 190, thus supporting the top portion 105 of the expandable cage 100.

Furthermore, in some embodiments, when the top portion 105 is engaged or mated with the bottom portion 110, the slot 135 of the arms 130 receives the arms 140, thus restraining movement of the top portion with respect to the bottom portion in the anterior-posterior and medial-lateral directions, allowing only cephalad-caudal expansion or contraction of the top portion with respect to the bottom portion. In some embodiments, when the top portion 105 is engaged or mated with the bottom portion 110, the arms 125 are adjacent to the arms 145, thus restraining movement of the top portion with respect to the bottom portion in the anterior-posterior direction, but allowing for cephalad-caudal expansion or contraction of the top portion with respect to the bottom portion. Upon assembling the top portion 105 with the bottom portion 110, in an expanded position, the width of the expandable cage 100 is W1 and the length is L1. The final height, H1, of the expandable cage 100 is adjustable and determined by the height of the shim 190. In some embodiments, depending on the clinical circumstances, the expandable cage 100 may be implanted after being rotated 180 degrees in the vertical plane, such that the bottom portion 110 of the expandable cage is located cephalad to the top portion 105 of the expandable cage.

Thus, a lateral extrinsically expandable cage (e.g., the expandable cage 100) includes four main parts: the top portion 105, the bottom portion 110 configured to mate with the top portion, and two shims (e.g., two instances of the shim 190 or two instances of the shim 195) that are inserted into the grooves 170 on the bottom portion, and hold the expandable cage in an expanded position of a variable height depending primarily on the height of the shims.

Figure 5B:
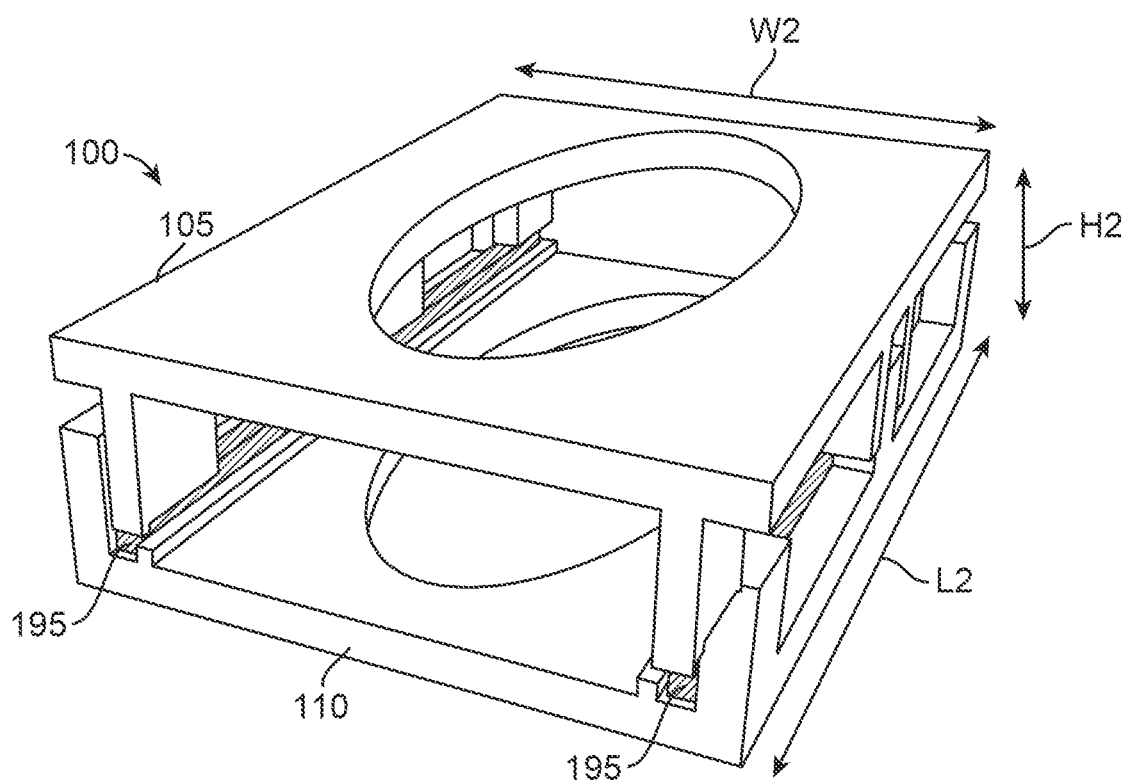
FIG. 5B is a perspective view depicting the top portion and the bottom portion of the expandable cage in an engaged position, with the shims inserted to expand the expandable cage to a second height, in accordance with an illustrative embodiment.

Referring to FIG. 5B, another perspective view depicting the expandable cage 100 in a final, fully engaged and expanded form after surgical implantation in a patient is shown, in accordance with illustrative embodiments. FIG. 5B is similar to FIG. 5A, but uses the shim 195 that is smaller in height than the shim 190 for adjusting the height of the expandable cage 100. Again, the top portion 105 is engaged or mated with the bottom portion 110, and the shim 195 is inserted into the grooves 170 for assembling the expandable cage 100. Upon assembly, the final height, H2, of the lateral extrinsically expandable cage (e.g., the expandable cage 100) of FIG. 5B is less than the final height, H1, of the lateral extrinsically expandable cage of FIG. 5A. However, the length, L2, of the expandable cage 100 of FIG. 5B is the same as the length, L1, of the expandable cage of FIG. 5A. Likewise, the width, W2, of the expandable cage 100 of FIG. 5B is the same as the width, W2, of the expandable cage of FIG. 5A. Thus, by varying the height of the shims (e.g., the shim 190 or the shim 195), the height, or the distance between the top portion 105 and the bottom portion 110, of the expandable cage 100 may be varied.

Figure 6A:
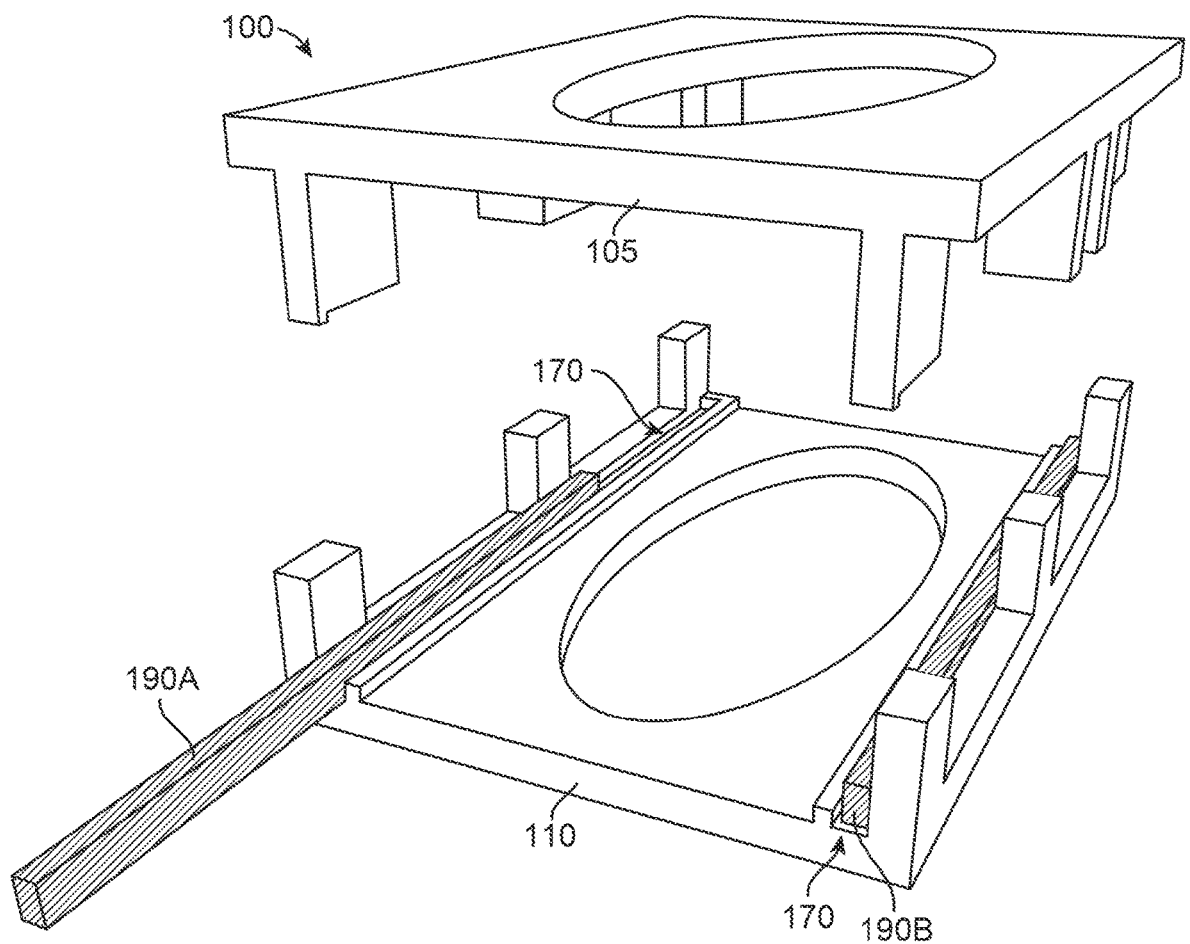
FIG. 6A is a perspective view depicting the shims in an assembling position within the bottom portion of the expandable cage, and with the top portion dis-engaged from the bottom portion, in accordance with an illustrative embodiment.
Figure 6B:
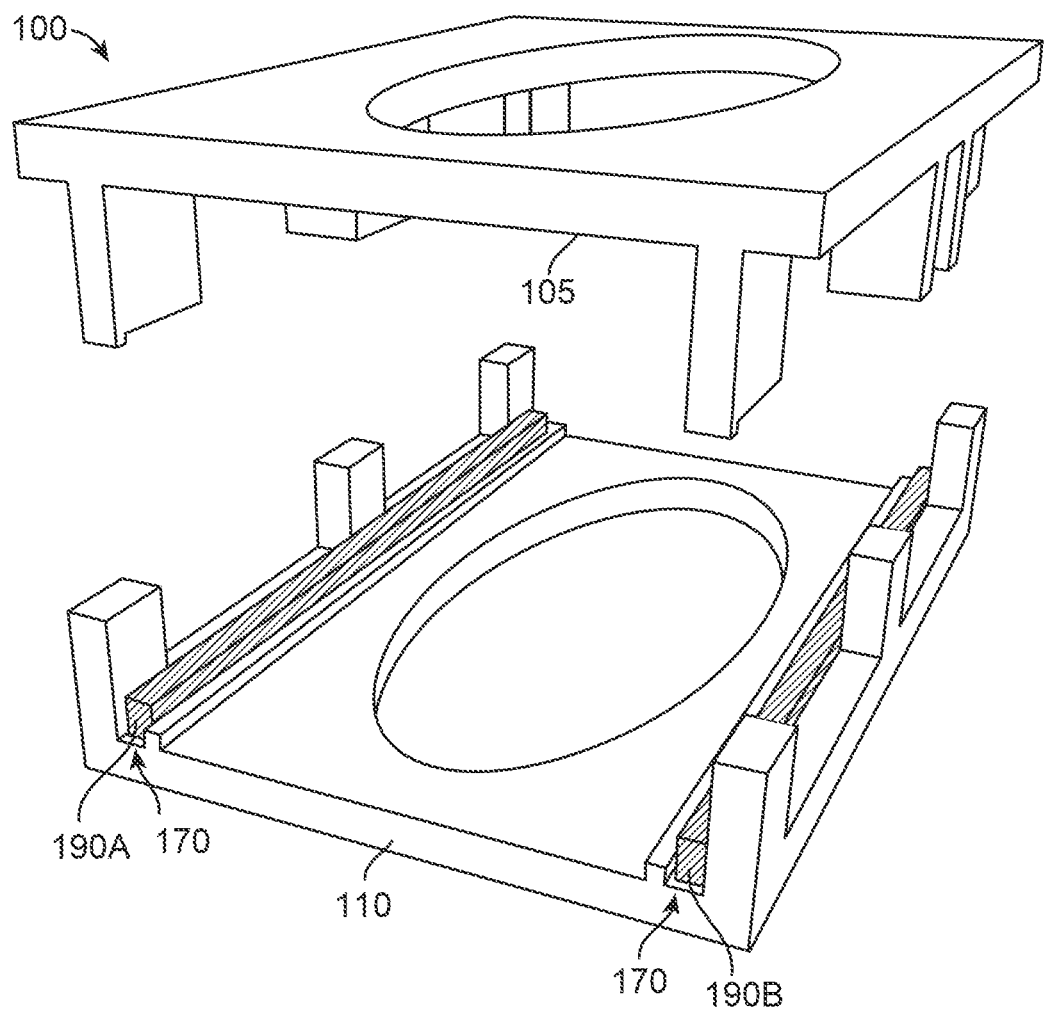
FIG. 6B is a perspective view depicting the shims in an assembled form within the bottom portion of the expandable cage, and with the top portion dis-engaged from the bottom portion, in accordance with an illustrative embodiment.

Turning to FIGS. 6A and 6B now, perspective views of the top portion 105 and the bottom portion 110 of the expandable cage 100 depicting insertion of shims 190A and 190B into the bottom portion are shown, in accordance with illustrative embodiments. Specifically, the perspective view of FIGS. 6A and 6B show the top portion 105 and the bottom portion 110 not engaging (e.g., separate from) each other to illustrate the insertion of the shims 190A and 190B into the bottom portion. It is to be understood that the top portion 105 is shown as being un-assembled from the bottom portion 110 to only illustrate the insertion of the shims 190A and 190B. In some embodiments, the shims 190A and 190B may indeed be inserted into the grooves 170 before assembling the top portion 105 to the bottom portion 110. In other embodiments, however, the top portion 105 may be assembled with the bottom portion 110 before the shims 190A and 190B are inserted into the grooves 170. As will be discussed below, an insertion and expansion device may be used to hold the top portion 105 in an expanded position relative to the bottom portion 110 to facilitate the insertion of the shims 190A and 190B.

FIG. 6A shows the shim 190A as partially inserted into the grooves 170 for purposes of illustration, and the shim 190B as fully inserted into the grooves. FIG. 6B shows both the shims 190A and 190B as fully inserted into the grooves 170. Furthermore, in some embodiments, the shims 190A and 190B are identical to each other, and are configured to be received (e.g., by sliding) within the grooves 170. In other embodiments, the shims 190A and 190B may be of varying configurations. Also, in some embodiments, each of the grooves 170 may be of varying configurations (e.g., of varying widths). In those instances, the shims 190A and 190B may be of different configurations to correspond to the configuration of the respective one of the grooves 170 in which they are configured to be received.

Figure 7:
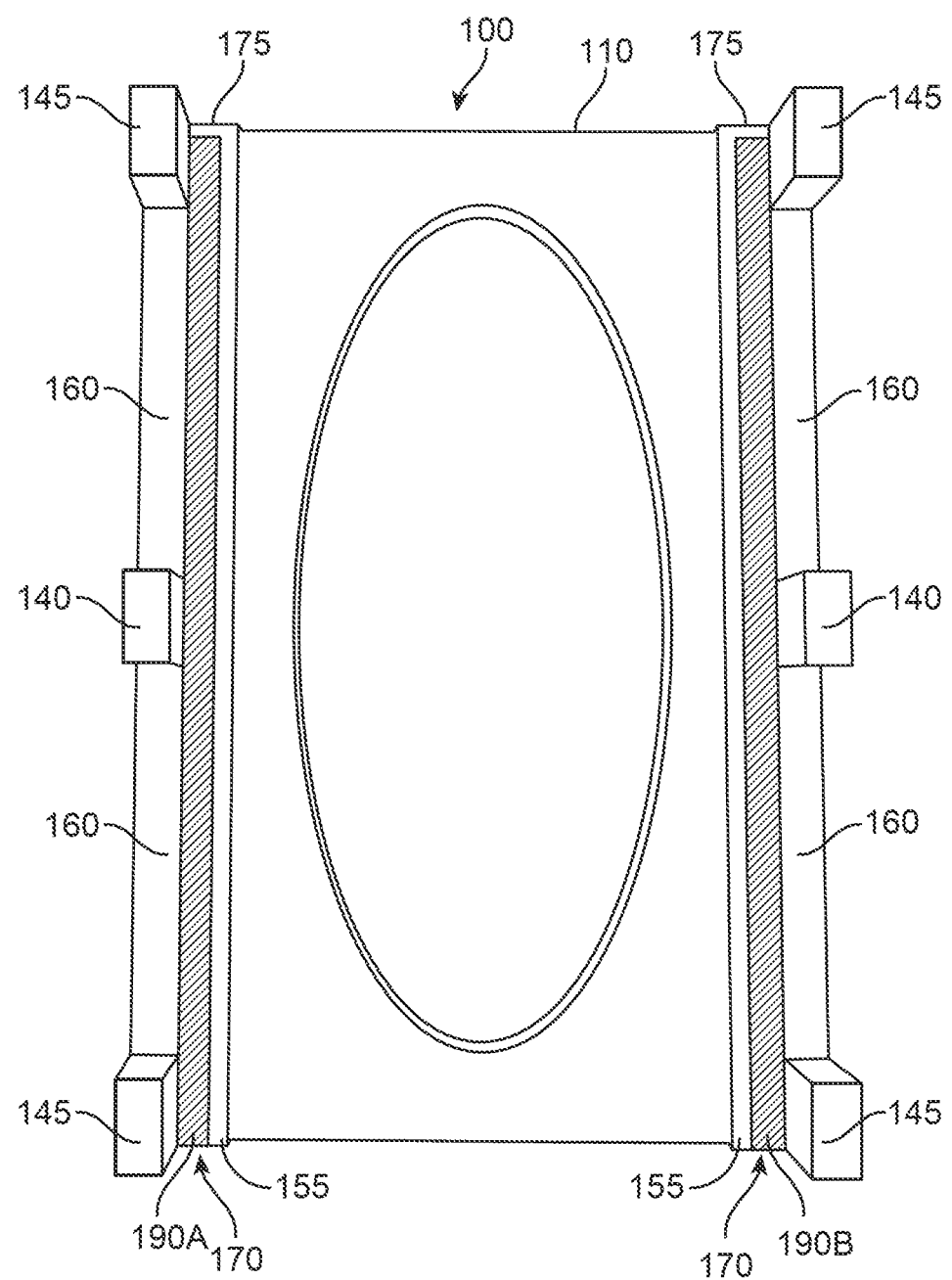
FIG. 7 is a top perspective view depicting the shims in the assembled form in the bottom portion of the expandable cage, in accordance with an illustrative embodiment.

Turning now to FIG. 7, a perspective view of the bottom portion 110 is shown, in accordance with an illustrative embodiment. The perspective view of FIG. 7 shows the shims 190A and 190B inserted into the grooves 170. Specifically, the shims 190A and 190B may be inserted into the grooves 170 by sliding the shims via the openings 180 into the grooves until the shims make contact with the end projections 175. Thus, the shims 190A and 190B sit within the grooves 170, and are bound by the outward projections 155 and 160, the end projections 175, and the lip 185 of the top portion 105 upon assembly. The outward projections 155 and 160, the end projections 175, and the lip 185 constrain the movement of the shims 190A and 190B within the grooves 170. Although the shims 190A and 190B have been shown in the present embodiment as extending across the entire (or substantially entire) length (e.g., length, L1 and L2) of the expandable cage 100, in other embodiments, either or both of those shims may be smaller in length and may span only a portion of the length of the expandable cage. Furthermore, to accommodate the shims 190A and 190B that are only a portion of the length of the expandable cage 100, the grooves 170 may or may not be of correspondingly smaller length. In some embodiments, each of the grooves 170 may be of different lengths to accommodate the shims 190A and 190B that are of different lengths. Thus, various configurations of the shims 190A and 190B, as well as of the grooves 170 are contemplated and considered within the scope of the present disclosure.

Figure 8A:
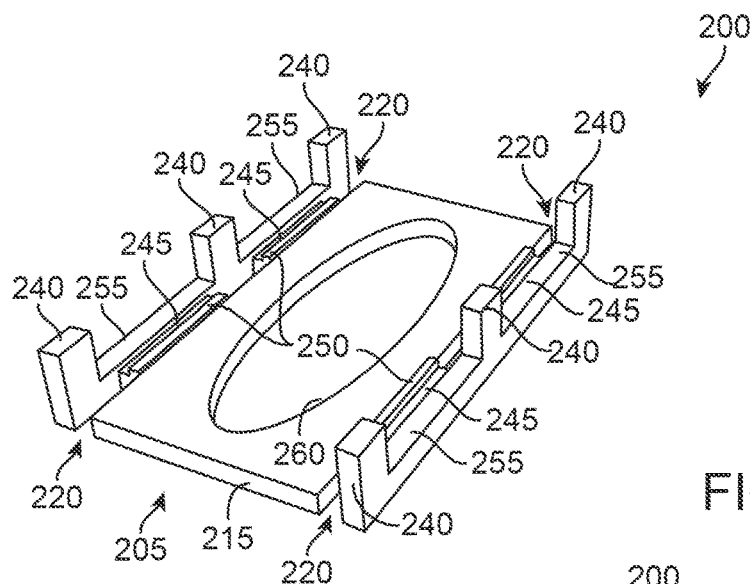
FIG. 8A is a perspective view depicting the bottom portion of the expandable cage, in accordance with another illustrative embodiment.
Figure 8B:
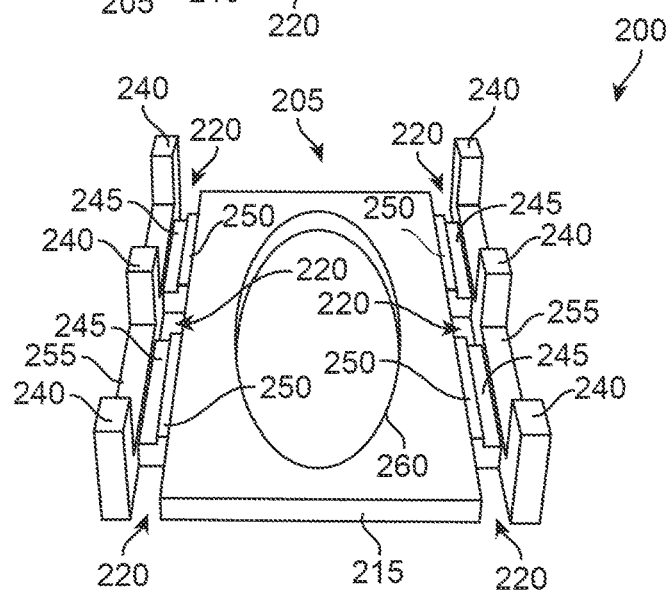
FIG. 8B is another perspective view depicting the bottom portion of the expandable cage of FIG. 8A, in accordance with another illustrative embodiment.
Figure 8C:
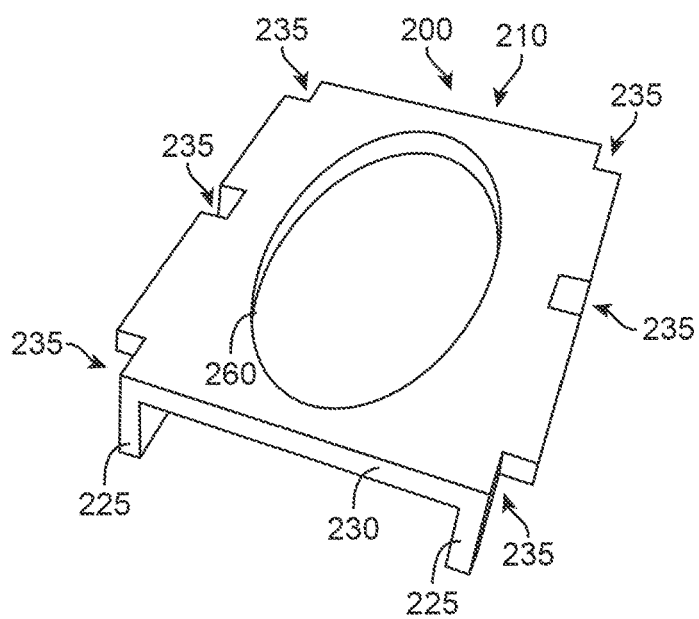
FIG. 8C is a perspective view depicting the top portion of the expandable cage, in accordance with another illustrative embodiment.

Referring now to FIGS. 8A-8C, perspective views depicting an alternative embodiment of an expandable cage 200 are shown, in accordance with illustrative embodiments. Specifically, FIGS. 8A and 8B show a perspective view of a bottom portion 205 and FIG. 8C shows a perspective view of a top portion 210 of a lateral extrinsically expandable cage (e.g., the expandable cage 200), in accordance with illustrative embodiments.

Referring to FIGS. 8A and 8B in conjunction with FIG. 8C now, the bottom portion 205 includes a lower section 215 having cutouts 220 that accommodate arms 225 (only two of which are visible in FIG. 8C) of the top portion 210. Likewise, in some embodiments, upper section 230 of the top portion 210 includes cutouts 235 that accommodate arms 240 of the bottom portion 205. In some embodiments, the shape and size of the cutouts 220 and the cutouts 235 may be varied to correspond to the shape and size of the arms 225 and the arms 240. In some embodiments, the shape and/or size of the cutouts 220 may be different from the shape and/or size of the cutouts 235 to correspond to the varying shape and/or size of the arms 225 and the arms 240. Further, although six of the arms 225 and six of the arms 240 have been shown in the present disclosure, in other embodiments, greater than or fewer than six arms may be used for each of the arms 225 and the arms 240. The number of the cutouts 220 and the cutouts 235 may vary based upon the number of the arms 225 and the arms 240, respectively, that those cutouts are configured to receive.

Furthermore, in at least some embodiments, grooves 245 may be provided on the bottom portion 205. The grooves 245 may be provided on the lower section 215, bordered by walls 250 and 255 that project outwards from the lower section. In contrast to the grooves 170 that extend the entire (or substantially entire) length of the expandable cage 100, the grooves 245 are configured to extend only a portion of the length of the expandable cage 200. Specifically, as shown in FIGS. 8A and 8B, the grooves 245 on each side of the expandable cage 200 include two grooves separated by the cutouts 220. The grooves 245 may be used to receive shims, as discussed above, for expanding the height of the expandable cage 200 upon assembly. The expandable cage 200 also includes an opening 260, which is similar to the opening 150, and configured to receive a bone graft promoting material. The shape, size, and other configuration of the opening 260 may vary from one embodiment to another, and in some embodiments, the opening may be absent.

By virtue of using the cutouts 220 and the cutouts 235, maximal contraction of the expandable cage 200 may be achieved, such that the overall height of the expandable cage is further reduced (compared to the maximally contracted height of the expandable cage 100), thereby facilitating easier insertion of the expandable cage into the spinal cavity. The cutouts 220 and the cutouts 235 also reduce the amount of material that is used for constructing the expandable cage 200, thereby reducing the overall cost of manufacturing the expandable cage.

Figure 9A:
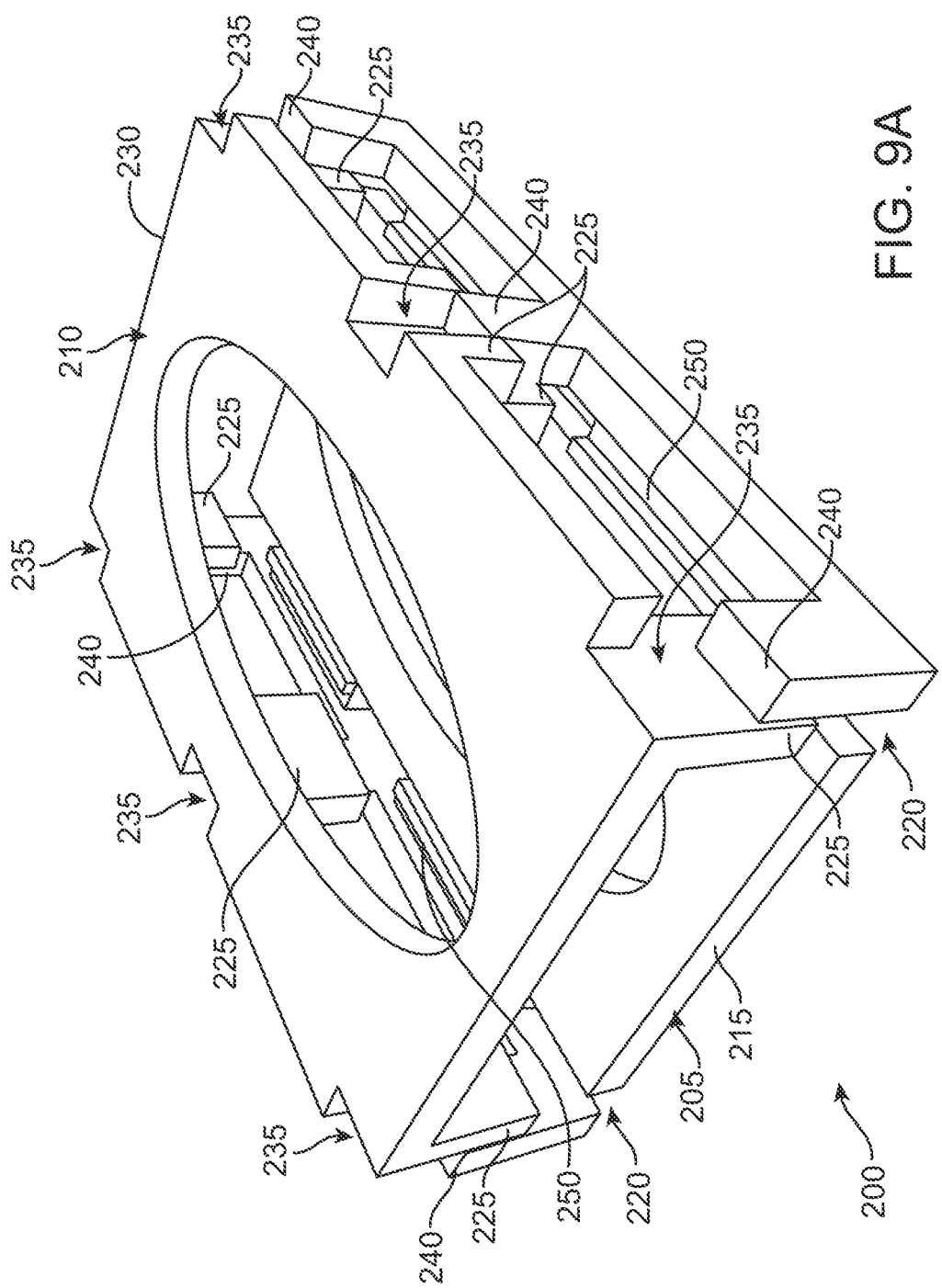
FIG. 9A is a perspective view depicting the top portion and the bottom portion of the expandable cage in an engaged position, with the expandable cage expanded and prior to inserting the shims, in accordance with another illustrative embodiment.
Figure 9B:
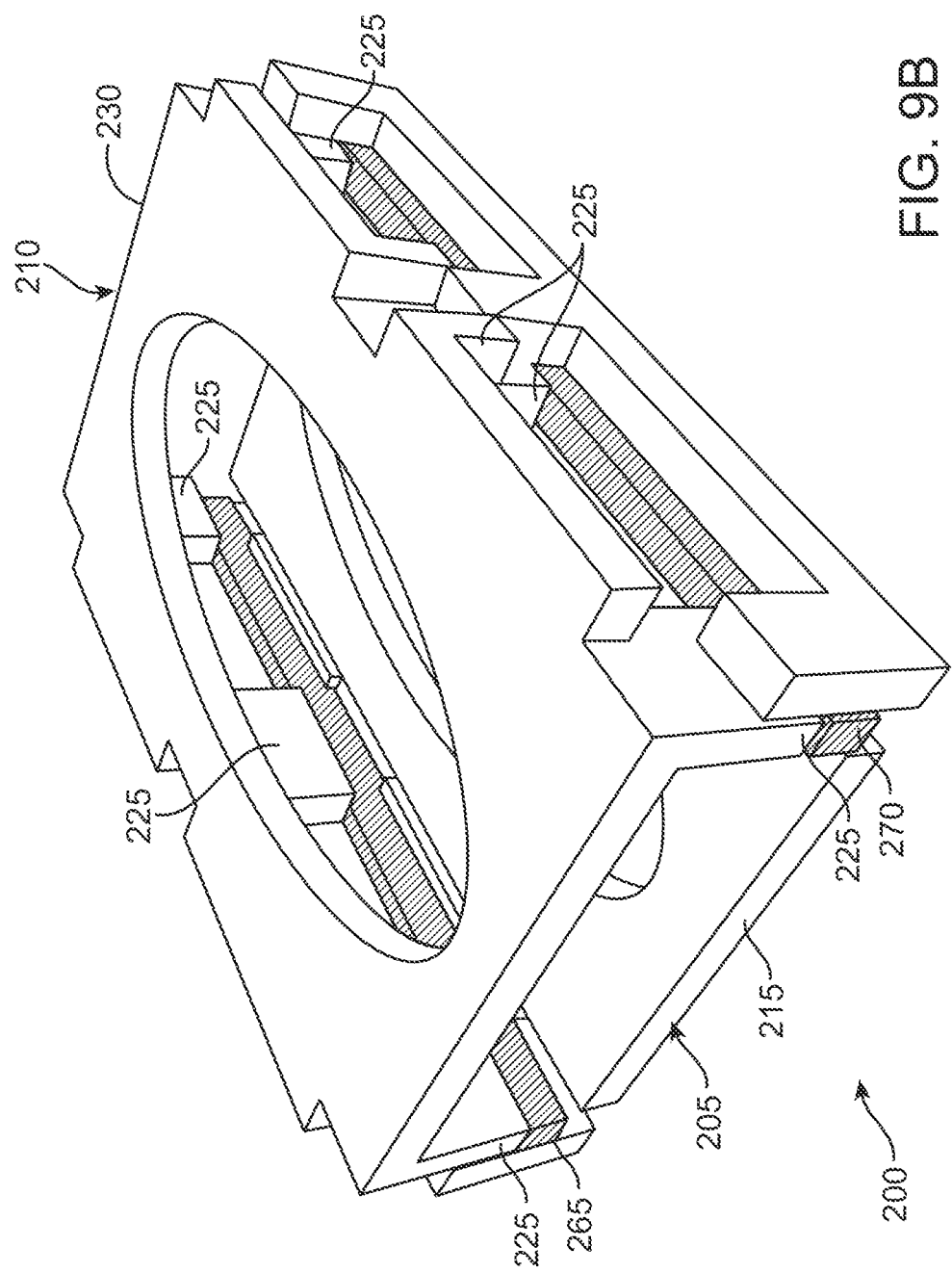
FIG. 9B is a perspective view depicting the top portion and the bottom portion of the expandable cage in an engaged position, with the expandable cage expanded and with the shims inserted, in accordance with another illustrative embodiment.

Turning now to FIGS. 9A and 9B, assembly of the expandable cage 200 is depicted, in accordance with at illustrative embodiment. Specifically, FIG. 9A shows the expandable cage 200 in an engaged position prior to shim insertion, while FIG. 9B shows the expandable cage in the engaged position with the shims inserted. As shown in FIGS. 9A and 9B, the top portion 210 is configured to engage or mate with the bottom portion 205. Specifically, in some embodiments, the arms 225 of the top portion 210 are received within the cutouts 220, and the arms 240 are received within the cutouts 235 to facilitate engagement of the top portion with respect to the bottom portion. Further, the grooves 245 are designed to accommodate shims 265 and 270 (See FIG. 9B). The configuration of FIG. 9A shows the top portion 210 of the expandable cage 200 assembled to the bottom portion 205 thereof, but without the assembly of the shims 265 and 270, while FIG. 9B shows the shims assembled within the expandable cage.

Thus, FIG. 9B shows a perspective view of the expandable cage 200, now with the addition of the shims 265 and 270, in accordance with an illustrative embodiment. The top portion 210 is shown as engaging or mated with the bottom portion 205. In some embodiments, the grooves 245 accommodate the shims 265 and 270. In some embodiments, the shims 265 and 270 sit within the grooves 245, such that an inferior-most surface (e.g., a bottom surface) of the shims 265 and 270 rests on the superior-most surface (e.g., a top surface) of the lower section 215 of the bottom portion 205. In turn, the inferior-most surface (e.g., a bottom surface) of the arms 225 of the top portion 210 rest on a superior-most surface (e.g., a top surface) of the shims 265 and 270, thus, holding the expandable cage 200 in a mechanically stable expanded configuration. It is to be understood that although each of the grooves 245 are configured as two smaller grooves separated by the cutouts 220, in some embodiments, the shims 265 and 270 may be configured to span the entire (or substantially entire length of the bottom portion 205. In other embodiments, smaller shim portions of the shims 265 and 270 spanning only the length of each respective one of the grooves 245 may be used.

Furthermore, in some embodiments, the arms 225 of the top portion 210 may be configured to articulate via a hinge or similar rotatory component relative to the upper section 230 of the top portion. Likewise, the arms 240 of the bottom portion 205 may be configured to articulate relative to the lower section 215 of the bottom portion. By articulating the arms 225 and the arms 240, shims (e.g., the shims 265 and 270) of different heights anteriorly and posteriorly may be placed, thereby resulting in an expandable cage (e.g., the expandable cage 200) with a taller height anteriorly than posteriorly, or a taller height posteriorly than anteriorly, which may result in the expandable cage assuming a lordotic or kyphotic configuration. Such a configuration may in turn enable a surgeon to control, to some degree, a patient's sagittal alignment during an operation.

Figure 10:
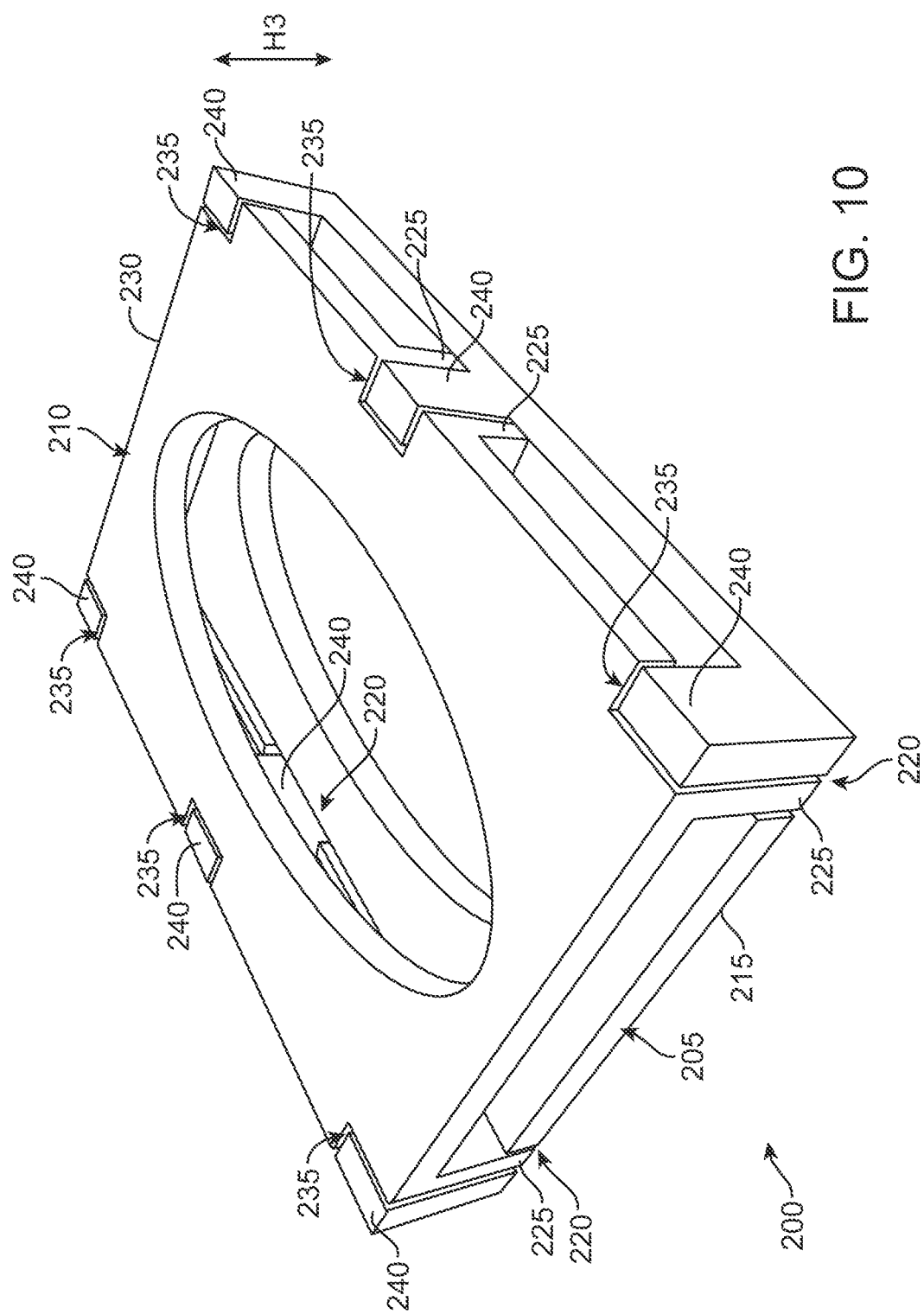
FIG. 10 is a perspective view depicting the top portion and the bottom portion of the expandable cage in an engaged position, with the shims removed and the expandable cage maximally contracted in height, in accordance with another illustrative embodiment.

Turning now to FIG. 10, a perspective view of the expandable cage 200 in a maximally contracted position is shown, in accordance with an illustrative embodiment. The top portion 210 is shown engaging or mating with the bottom portion 205. In some embodiments, and as discussed above, the lower section 215 of the bottom portion 205 includes the cutouts 220 that accommodate the arms 225 of the top portion 210. Likewise, the cutouts 235 accommodate the arms 240 of the bottom portion 205. The cutouts 220 and 235 serve the purpose of allowing the expandable cage 200 to contract or collapse to a shortest possible height, H3, which facilitates surgical insertion, for example, into a relatively collapsed intervertebral disk space. In comparison to the expandable cage 100, the expandable cage 200 allows for a greater height contraction.

Specifically, referring back to FIG. 2 above, when the top portion 105 mates with the bottom portion 110 of the expandable cage 100, in a maximally contracted position, the inferior-most surface (e.g., a bottom surface) of the arms 125 and 130 come into contact with the superior-most surfaces (e.g., a top surface) of the outward projections 155, as well as the end projections 175. Likewise, the superior-most surfaces (e.g., a top surface) of the arms 140 and 145 contact the inferior-most surface (e.g., the bottom surface 120) of the top portion 105, thus limiting the amount of maximal contraction of the expandable cage 100. By virtue of providing the cutouts 220 and 235 in the expandable cage 200, the arms 225 and 240, respectively, are not limited by the outward projections 155, 160, thereby enabling the expandable cage 200 to achieve a smaller height profile compared to the expandable cage 100.

Referring now to FIG. 11, a perspective view of a bottom portion 275 and an alternative embodiment of a top portion 280 of a lateral extrinsically expandable cage (e.g., expandable cage 285) is shown, in accordance with an illustrative embodiment. To the extent that the expandable cage 285 is similar to the expandable cage 100, only the differences are described herein. The top portion 280 includes arms 290 that are configured as outward projections from a bottom surface 295 of the top portion. In some embodiments, the arms 290 are configured as a single continuous piece of material that runs the length L3 of the top portion 280. The bottom portion 275 is similar in configuration to the bottom portion 110, and is therefore, not described here again.

In some alternative embodiments, the arms 290 may articulate via a hinge or similar rotatory component relative to the bottom surface 295 of the top portion 280. In this manner, shims (not shown, depicted later in FIGS. 12B and 12C) of different heights may be placed to result in an expandable cage (e.g., the expandable cage 285) with a taller height anteriorly than posteriorly, or a taller height posteriorly than anteriorly, which in turn may result in the expandable cage assuming a lordotic or kyphotic configuration. Such a configuration may enable the surgeon to control, to some degree, a patient's sagittal alignment.

Figure 12A:
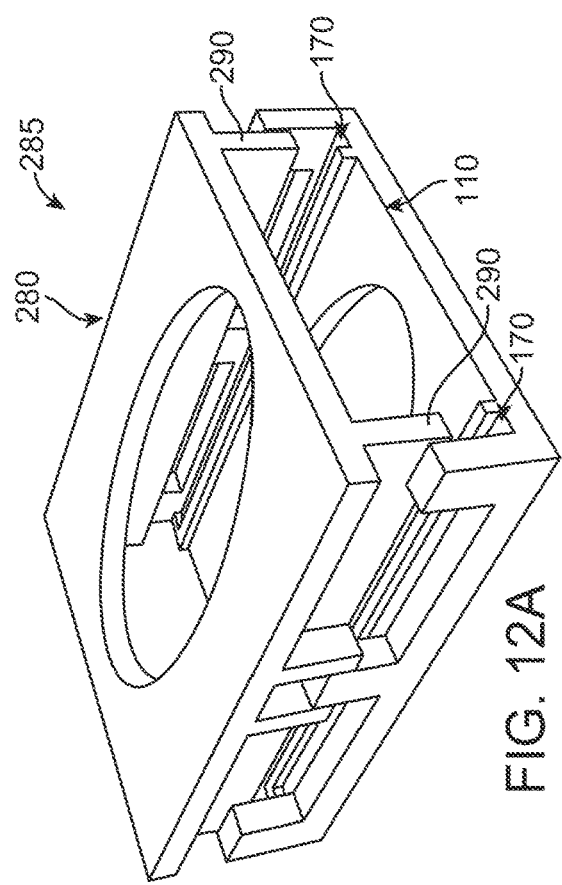
FIG. 12A is a perspective view depicting the top portion and the bottom portion of the expandable cage in an engaged position, with the expandable cage expanded and prior to inserting the shims, in accordance with yet another illustrative embodiment.
Figure 12B:
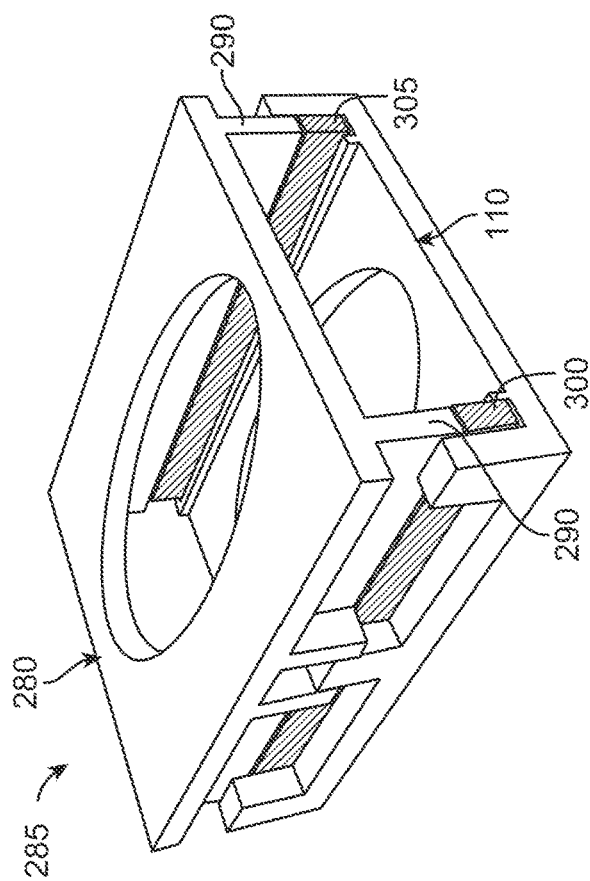
FIG. 12B is a perspective view depicting the top portion and the bottom portion of the expandable cage in an engaged position, with the expandable cage expanded and the shims inserted, in accordance with yet another illustrative embodiment.
Figure 12C:
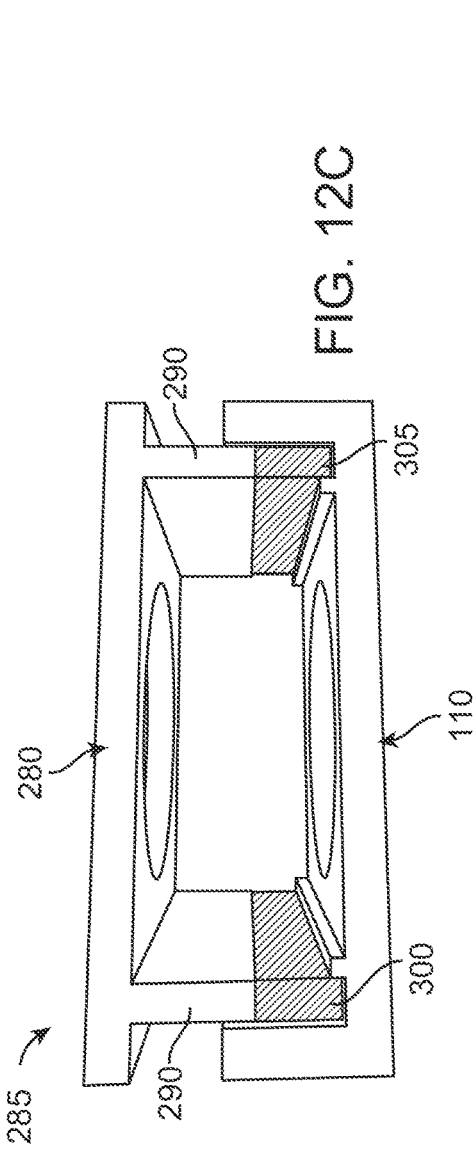
FIG. 12C is a side perspective view depicting the top portion and the bottom portion of the expandable cage in an engaged position, with the expandable cage expanded and the shims inserted, in accordance with yet another illustrative embodiment.

Turning now to FIGS. 12A-12C, perspective views depicting the top portion 280 and the bottom portion 275 in the expandable cage 285 are shown, in accordance with illustrative embodiments. Specifically, FIG. 12A is a perspective view depicting the top portion 280 and the bottom portion 275 of the expandable cage 285, with the top portion mated to or engaging with the bottom portion before the insertion of the shims, in accordance with an illustrative embodiment. The grooves 170 on the bottom portion 275 are configured to receive the shims to hold the expandable cage 285 in the expanded configuration. FIG. 12B is a perspective view depicting the top portion 280 and the bottom portion 275 of the expandable cage 285 as shown in FIG. 12A, but with shims 300 and 305 inserted into the grooves 170, in accordance with an illustrative embodiment. In some embodiments, upon insertion of the shims 300 and 305, the inferior-most surface (e.g., a bottom surface) of the arms 290 rests on the superior-most surface (e.g., a top surface) of the shims 300 and 305 along the entire length of said surfaces, thus holding the expandable cage 285 in an expanded configuration.

FIG. 12C is a side perspective view depicting the top portion 280 and the bottom portion 275 of the expandable cage 285 with the shims 300 and 305 inserted, as shown in FIG. 12B, in accordance with an illustrative embodiment. Again, in some embodiments, the inferior-most surface (e.g., a bottom surface) of the arms 290 rests on the superior-most surface (e.g., a top surface) of the shims 300 and 305 along the entire length of said surfaces, thus holding the expandable cage 285 in an expanded configuration. Upon assembly, the shim 305 may be the anterior shim, and the shim 300 may be the posterior shim, or vice-versa. In some embodiments, the shims 300 and 305 are of identical height, resulting in a final overall cage height that is the same both anteriorly and posteriorly, thereby resulting in a level or parallel cage.

Referring back to the description of an alternative embodiment with a hinged articulation between the arms 290 relative to the bottom surface 295 of the top portion 280, as described in FIG. 11 above, it may be possible to place a shim (e.g., the shim 305) that is of a different height than the other shim (e.g., the shim 300). If the shim 305 is taller in height than the shim 300, the expandable cage 285 is a lordotic cage. If the shim 300 is taller in height than the shim 305, the expandable cage 285 is a kyphotic cage. A surgeon may use different shim heights to produce a lordotic or kyphotic lateral extrinsically expandable cage of differing sagittal dimensions, which would allow the surgeon to control, to some degree, a patient's sagittal alignment during an operation. In an alternative embodiment, the tolerance between the arms 290, 140, and 145 may be designed such that different shim heights may produce a lordotic or kyphotic cage in the absence of a hinge or other articulation between the arms and the upper or bottom sections of the cage.

Figure 13:
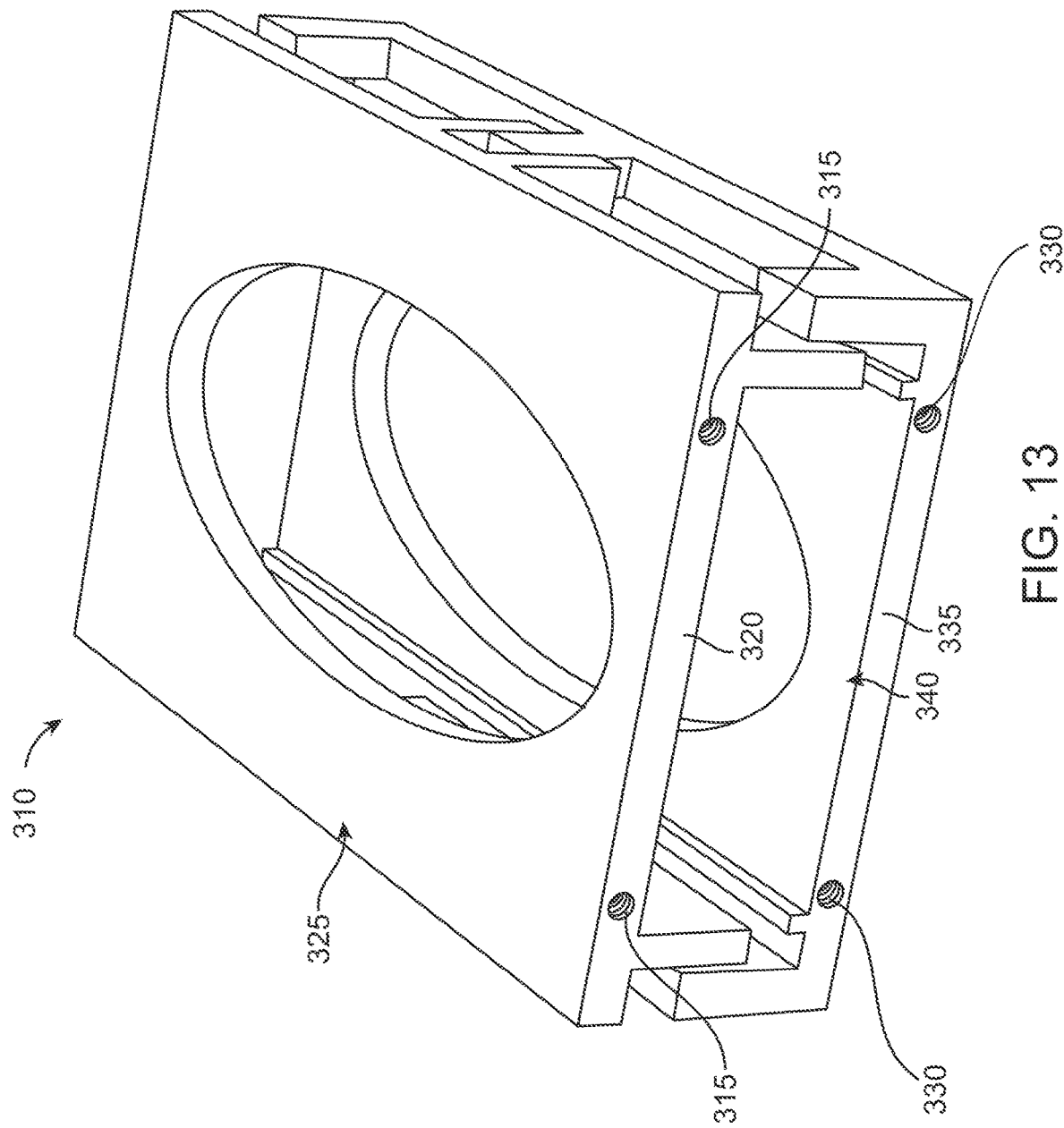
FIG. 13 is a perspective view depicting the top portion and the bottom portion of the expandable cage having features configured to attach a cage insertion and expansion device, in accordance with an illustrative embodiment.

Turning now to FIG. 13, a perspective view depicting an alternative embodiment of an expandable cage 310 is shown, in accordance with an illustrative embodiment. The expandable cage 310 is similar to the expandable cage 100, the expandable cage 200, and the expandable cage 285. The expandable cage 310 also includes two threaded holes 315 on a sidewall 320 of top portion 325 that correspond with two threaded holes 330 on a sidewall 335 on a bottom portion 340. The threaded holes 315 and 330 are configured to attach to a cage insertion and expansion device (not shown) for keeping the top portion 325 in an expanded position relative to the bottom portion 340 until the shims (not shown) are inserted. Although only two of the threaded holes 315 and 330 are shown, in some embodiments, there may be more or fewer number of holes in the top portion 325 and the bottom portion 340. Further, the threaded holes 315 and 330 may or may not be threaded. Rather, other configurations may be used to attach the expandable cage 310 to a cage insertion and expansion device (not shown). Moreover, the location of the threaded holes 315 and 330 may vary in other embodiments. For example, in some embodiments, the threaded holes 315 may be located at any point(s) along the sidewall 320 of the top portion 325 and the threaded holes 330 may correspondingly be placed on the sidewall 335 of the bottom portion 340. In some embodiments, the threaded holes 315 and 330 may be provided on other parts of the expandable cage 310 for attaching the cage insertion and expansion device. In some embodiments, the means of attachment of a cage insertion and expansion device may be integrated with the expandable cage 310, and may be comprised of any design that allows for attachment of the cage insertion and expansion device. In some embodiments, the insertion device may be separate from the expansion device.

Figure 14A:
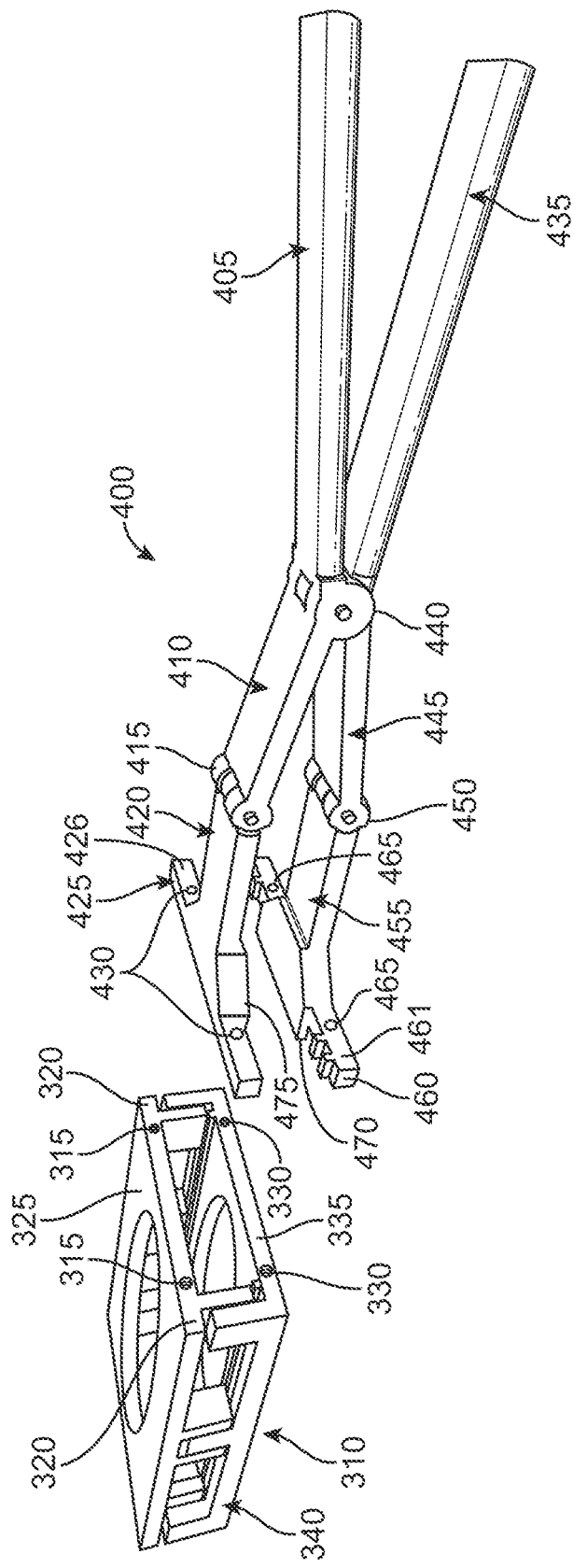
FIG. 14A is a perspective view depicting the expandable cage and the insertion and expansion device in an assembly position, in accordance with an illustrative embodiment.

Turning now to FIG. 14A, a perspective view depicting the expandable cage 310 and an insertion and expansion device 400 is shown, in accordance with illustrative embodiments. As discussed above with respect to FIG. 13, in some embodiments, the expandable cage 310 includes the threaded holes 315 on the sidewall 320 of the top portion 325. The threaded holes 315 correspond with the threaded holes 330 on the sidewall 335 on the bottom portion 340. The threaded holes 315 and the threaded holes 330 are configured to attach to the cage insertion and expansion device 400 for keeping the top portion 325 in an expanded position or configuration relative to the bottom portion 340 until the shims (not shown) are inserted. In some embodiments, the insertion and expansion device 400 includes an upper handle 405 that joins at an angle to arm 410, which in turn is connected to arm 420 via hinge 415. The insertion and expansion device also includes a lower handle 435 that joins at an angle to arm 445, which in turn is connected to arm 455 via hinge 450. In some embodiments, the upper handle 405 articulates relative to the lower handle 435 via a hinge 440. In some embodiments, the arm 420 includes a part 425 that has a face 426 that faces away from the expandable cage 310 and towards the surgeon, and an opposite face (not shown) that faces towards the expandable cage and may be configured to press against the sidewall 320 of the top portion 325 of the expandable cage. Likewise, the arm 455 includes a part 460 that has a face 461 that faces away from the expandable cage 310 and towards the surgeon, and an opposite face (not shown) that faces away from the surgeon and may be configured to press against the sidewall 335 of the bottom portion 340 of the expandable cage.

The pressing together of the insertion and expansion device 400 against the expandable cage 310 facilitates attachment of the insertion and expansion device to the expandable cage, as described below in more detail. In some embodiments, the part 425 includes holes 430 that are positioned in line with the threaded holes 315, and the part 460 includes holes 465 that are positioned in line with the threaded holes 330. The holes 430 and 465 are used to attach the insertion and expansion device 400 to the expandable cage 310, as discussed in greater detail in FIGS. 14B-14G. In some embodiments, the arm 420 may include an extension 475 and the arm 455 may include an extension 470. In some embodiments, the extensions 470 and 475 may fit within the expandable cage 310 and be employed to assist in the expansion of the expandable cage, as discussed in greater detail in FIGS. 14B-14F.

Figure 14B:
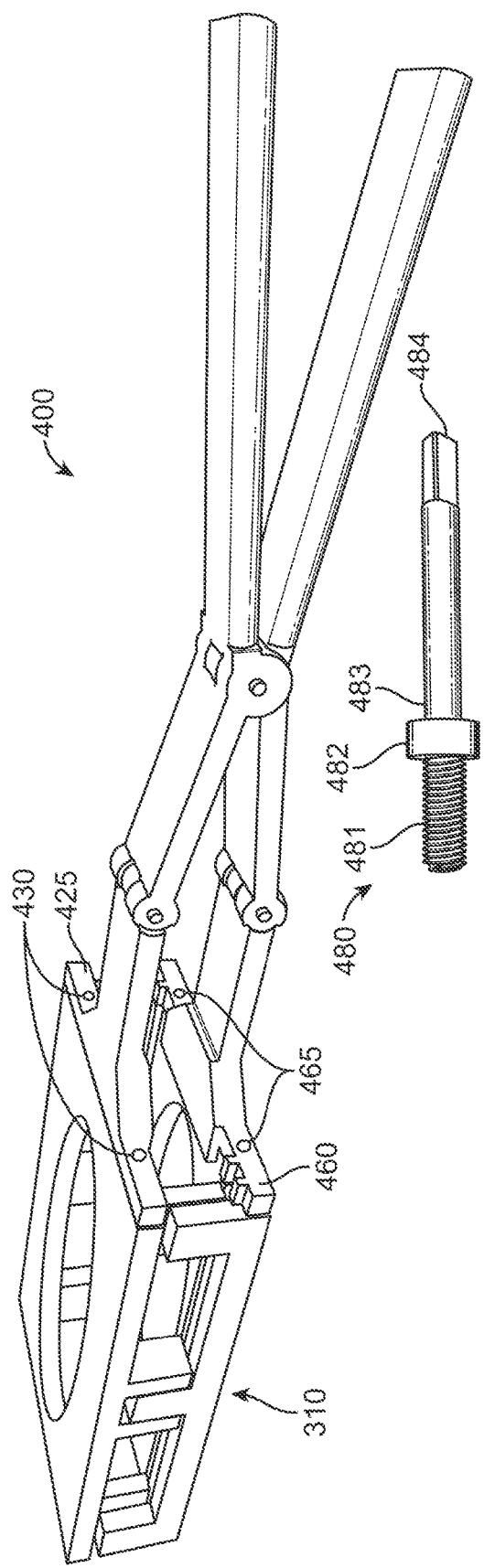
FIG. 14B is a perspective view depicting the expandable cage and the insertion and expansion device in an assembled position, prior to insertion of fasteners, in accordance with an illustrative embodiment.
Figure 14C:
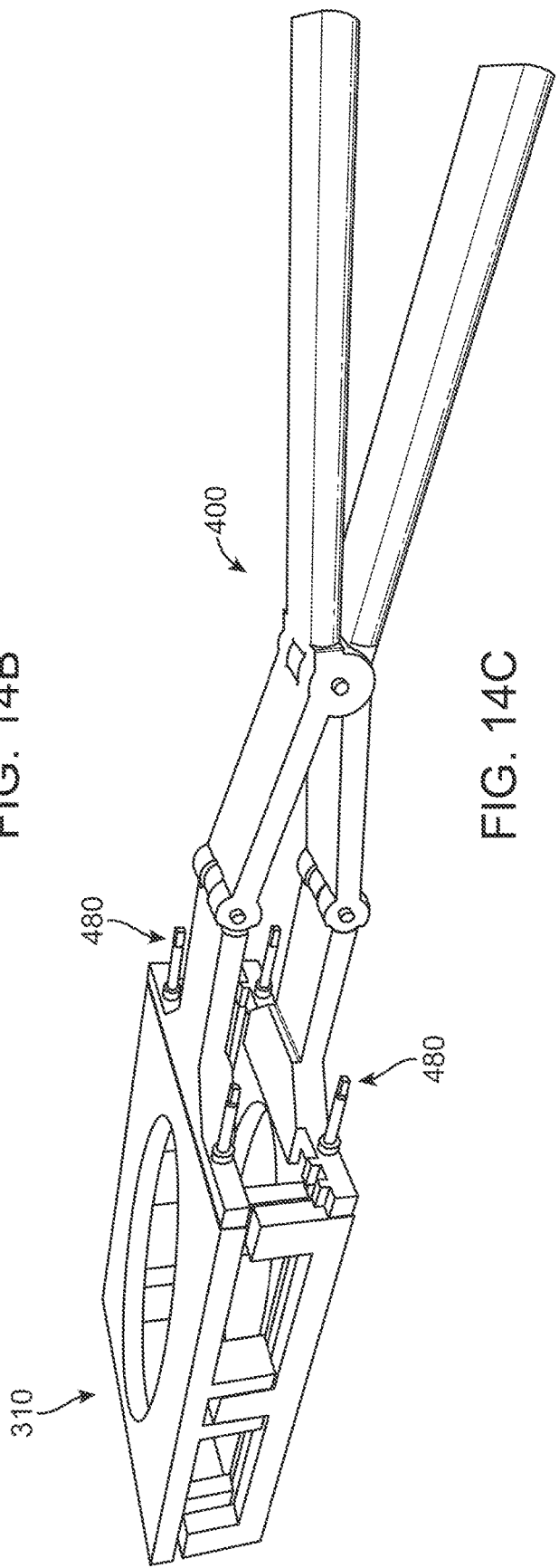
FIG. 14C is a perspective view depicting the expandable cage and the insertion and expansion device in an assembled position, with fasteners securing the expandable cage to the insertion and expansion device, in accordance with an illustrative embodiment.

Turning now to FIG. 14B and FIG. 14C, perspective views depicting the attachment of the insertion and expansion device 400 to the expandable cage 310 are shown, in accordance with illustrative embodiments. Specifically, FIG. 14B depicts the insertion and expansion device 400 sitting flush against the expandable cage 310, for receiving fasteners 480 through the holes 430 of the insertion and expansion device and the threaded holes 315 (not shown) of the expandable cage, as well as through the holes 465 of the insertion and expansion device and the threaded holes 330 (not shown) of the expandable cage. The fasteners 480 secure the insertion and expansion device 400 to the expandable cage 310. In some embodiments, the fasteners 480 include a threaded portion 481 which threads into the threaded holes 315 and 330 (See FIG. 14A) of the expandable cage 310, a collar 482 that presses or abuts against the part 425 and part 460 as the threaded portion 481 is advanced into the threaded holes 315 and 330 (Again, See FIG. 14A), and in so doing presses the part 425 and the part 460 tightly against the reciprocal sidewalls of the expandable cage 310. In some embodiments, the fasteners 480 include a shaft 483, and a terminal shaft portion 484 that corresponds to the configuration of a screwdriver or other similar insertion device (not shown) used to insert the fasteners 480 through the holes 430 and 465 and into the threaded holes 315 and 330.

FIG. 14C depicts the fasteners 480 having been inserted into the holes 430 and 465 of the insertion and expansion device 400 and threaded into the threaded holes 315 and 330 of the expandable cage 310, thus securing the insertion and expansion device to the expandable cage. Upon securing the insertion and expansion device 400 to the expandable cage 310, the expandable cage is now ready for insertion into the spine during the fusion operation. In some embodiments, four of the fasteners 480 are used, while in other embodiments, more or fewer fasteners may be used. Furthermore, in some embodiments, the configuration of the fasteners 480 may vary. For example, in some embodiments, one or more of the fasteners 480 need not be threaded. Rather, the fasteners 480 may be configured to attach the insertion and expansion device 400 to the expandable cage 310 via an interference fit or another connecting mechanism. Likewise, in some embodiments, the fasteners 480 need not always include one or more of the threaded portion 481, the collar 482, the shaft 483, and the terminal shaft portion 484. Rather, the fasteners 480 may be configured with greater, fewer or other components than those described herein. Additionally, in some embodiments, fastening mechanisms other than the fasteners 480 may be used for securing the insertion and expansion device 400 to the expandable cage 310. Once the expandable cage 310 is inserted into the spine and expanded to the desired height, and shims placed to hold the expandable cage in its expanded configuration, the fasteners 480 are removed. By removing the fasteners 480, the insertion and expansion device 400 may be disengaged from the expandable cage 310, such that the insertion and expansion device can be removed from the surgical area.

Figure 14D:
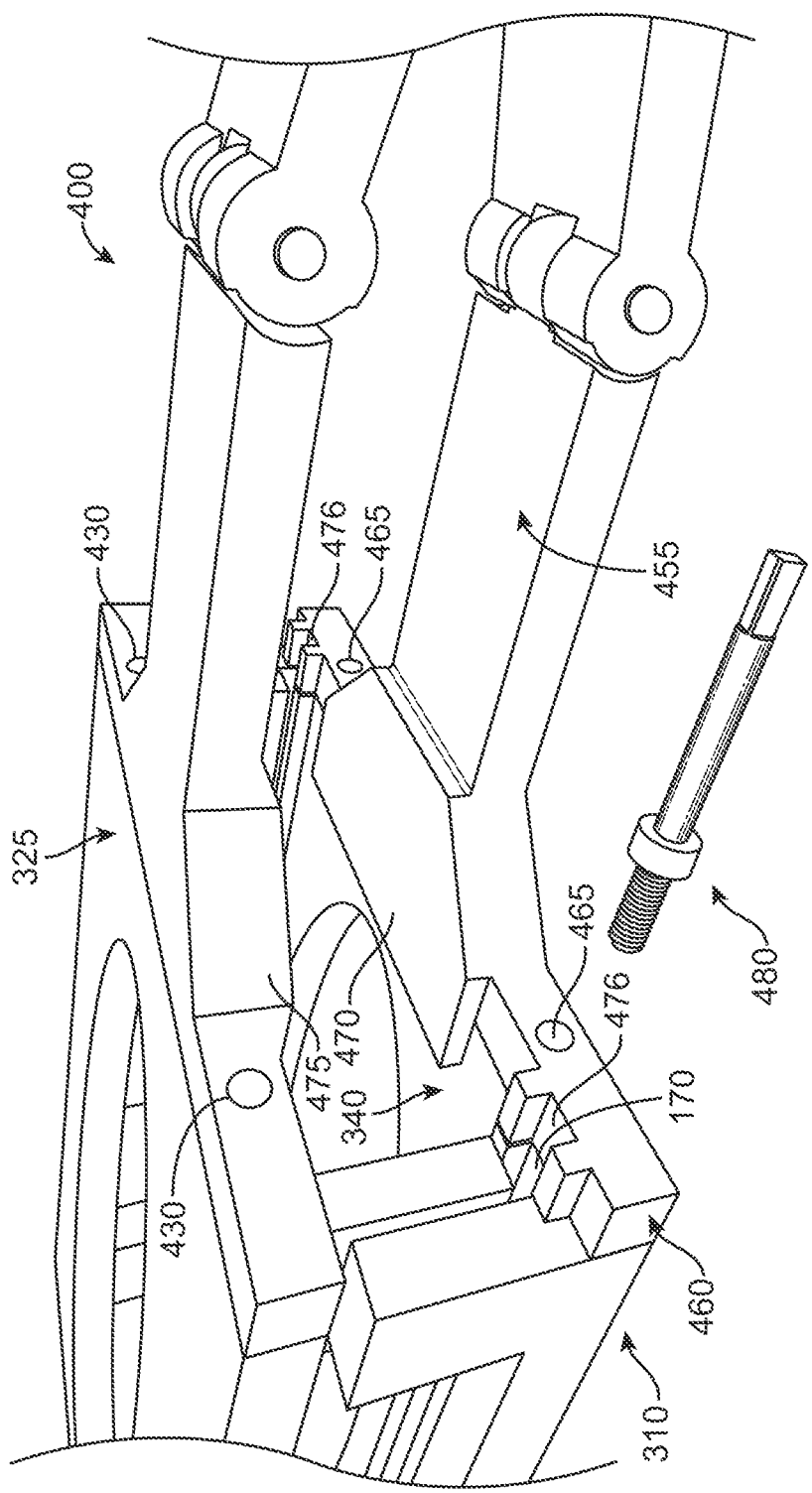
FIG. 14D is a perspective close-up partial view depicting the expandable cage and the insertion and expansion device in an assembled position, prior to insertion of fasteners, in accordance with an illustrative embodiment.

FIG. 14D is a close-up view of FIG. 14B, depicting a partial perspective view of the insertion and expansion device 400, and the expandable cage 310, in accordance with illustrative embodiments. In some embodiments, the holes 465 and 430 accommodate the fasteners 480 (a single instance of the fasteners 480 is shown here, but in this embodiment, four fasteners would be used, one for each of the holes 465 and 430). In some embodiments, the fasteners 480 are inserted through the holes 465 and into the threaded holes 330 of the expandable cage 310. Likewise, the fasteners 480 can be inserted through the holes 430 and into the threaded holes 315 of the expandable cage 310. As the fasteners 480 are tightened, the insertion and expansion device 400 is tightly pressed against the expandable cage 310, thus providing a rigid connection between the expandable cage and the insertion and expansion device. This allows the surgeon to insert the expandable cage 310 into the spine and expand the expandable cage to the desired height, prior to adding the shims (not shown). In some embodiments, the insertion and expansion device 400 includes the extension 470 and the extension 475 (partially shown). In some embodiments, the extensions 470 and 475 pass into expandable cage 310 and rest flush against the top and bottom portions of the expandable cage.

For example, as shown in FIG. 14D, the extension 470 is shown resting flush against an upward-facing (i.e., towards the patient's head) surface of the bottom portion 340 of the expandable cage 310, whereas the extension 475, which is only partially shown, is resting flush against the downwards-facing (i.e., towards the patient's feet) surface of the top portion 325 of the expandable cage 310. In some embodiments, the extensions 470 and 475 extend partially into the expandable cage 310, whereas in alternative embodiments, those extensions may extend along the entire length of the expandable cage. When the expandable cage 310 is inserted into the desired position in the spine during surgery, the insertion and expansion device 400 is used to expand the expandable cage to an extended configuration, and the extensions 470 and 475 assist in this expansion maneuver. Specifically, the extension 470 presses downwards on the upward-facing surface of the bottom portion 340 and the extension 475 presses upwards on the downwards-facing surface of the top portion 325, thus pressing the top portion away from the bottom portion, and facilitating expansion of the expandable cage 310 in a vertical direction. In some embodiments, the extensions 470 and 475 extend into the expandable cage 310 and serve as the primary connection between the insertion and expansion device 400 and the expandable cage 310, without relying on the fasteners 480. In some embodiments, the part 460 of the arm 455 includes a groove 476 that lines up with the grooves 170 (See FIGS. 1C, 2, 5A) of the expandable cage 310. When the expandable cage 310 is inserted into the spine during surgery and expanded using the insertion and expansion device 400, the shims are inserted into the grooves 170 (only one groove is visible in FIG. 14D) to hold the expandable cage in the expanded configuration. In some embodiments, the grooves 476 may be used by the surgeon to guide the shims into the grooves 170.

Turning now to FIG. 14E, a top perspective view of the expandable cage 310, the insertion and expansion device 400, and the fasteners 480 are shown in an assembling position, in accordance with illustrative embodiments. Specifically, FIG. 14E depicts the expandable cage 310 separate from the insertion and expansion device 400, with the fasteners 480 not yet securing the insertion and expansion device to the expandable cage. Referring to FIG. 14F, a top perspective view of the expandable cage 310, the insertion and expansion device 400, and the fasteners 480 are shown in an assembled position, with the fasteners securing the insertion and expansion device to the expandable cage.

Turning now to FIG. 14G and FIG. 14H, side perspective views of the expandable cage 310 attached to the insertion and expansion device 400 with the fasteners 480 are shown, in accordance with illustrative embodiments. In some embodiments, the insertion and expansion device 400 includes the upper handle 405 and the lower handle 435. FIG. 14G depicts the expandable cage 310 in its collapsed configuration, corresponding to an overall cage height H4, in which case the terminal ends (i.e., furthest from the expandable cage) of the upper handle 405 and the lower handle 435 are at their furthest distance from each other, represented by distance H4a in FIG. 14G. FIG. 14H depicts the expandable cage 310 in an expanded configuration, corresponding to overall cage height H5, in which case the terminal ends (i.e., furthest from the expandable cage 310) of the upper handle 405 and the lower handle 435 are closer to each other when compared to the distance H4a in FIG. 14G; this distance is shown as H5a. The height of the expandable cage 310 is, thus, adjustable—the closer the terminal ends of the upper handle 405 and the lower handle 435 are to each other, the taller (e.g., cage height) the expandable cage is, with the cage height expansion vertically within the limits of the cage component parameters.

Figure 15A:
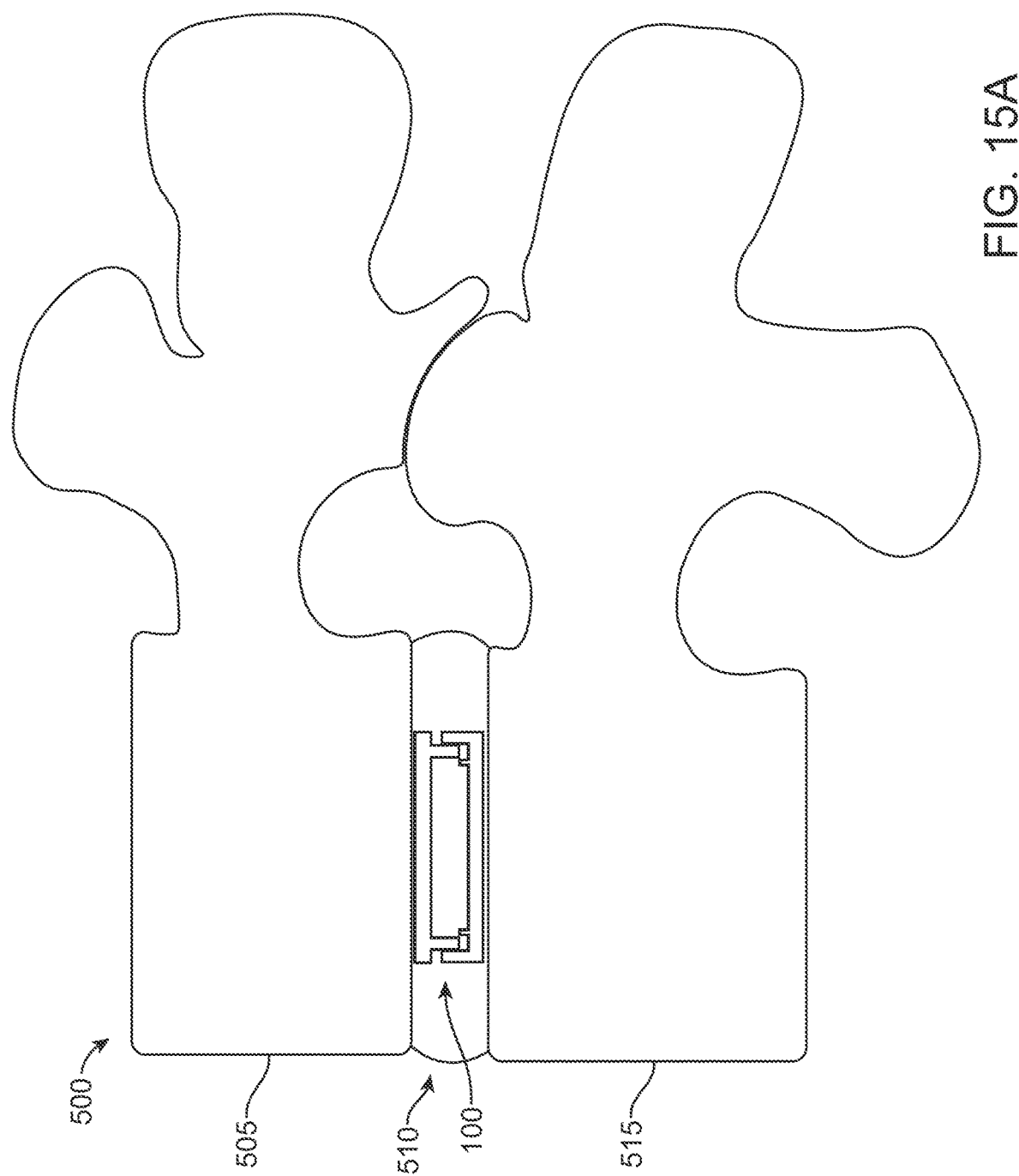
FIGS. 15A-15C are lateral or side views of a portion of a lumbar spine with the expandable cage inserted and positioned in an interbody space, with FIG. 15A depicting the expandable cage in the collapsed or contracted configuration, FIG. 15B depicting the expandable cage in an expanded configuration, and FIG. 15C depicting the expandable cage in an expanded configuration with the shims inserted for holding the expandable cage in an expanded configuration, in accordance with illustrative embodiments.

Turning now to FIG. 15A, a side or lateral view of a lumbar spine segment 500 is shown, in accordance with an illustrative embodiment. The lumbar spine segment 500 includes a cephalad vertebra 505, a caudal vertebra 515, and an intervertebral disk space 510. The expandable cage 100 is inserted into in the intervertebral disk space 510 after a diskectomy has been performed. As depicted in FIG. 15A, the expandable cage 100 is in a contracted or collapsed position. Although the expandable cage 100 is depicted in FIG. 15A as having certain dimensions, it is to be understood that in other embodiments, the dimensions of the expandable cage may vary based upon the size of the intervertebral disk space 510. For example, as depicted in FIG. 15A, although the expandable cage 100 does not cover the entire space of the intervertebral disk space 510, in other embodiments, the expandable cage 100 may be configured to be larger or smaller than depicted. For example, in some embodiments, the expandable cage 100 may vary in dimensions in either or both of the anterior-posterior and medial-lateral dimensions.

Figure 15B:
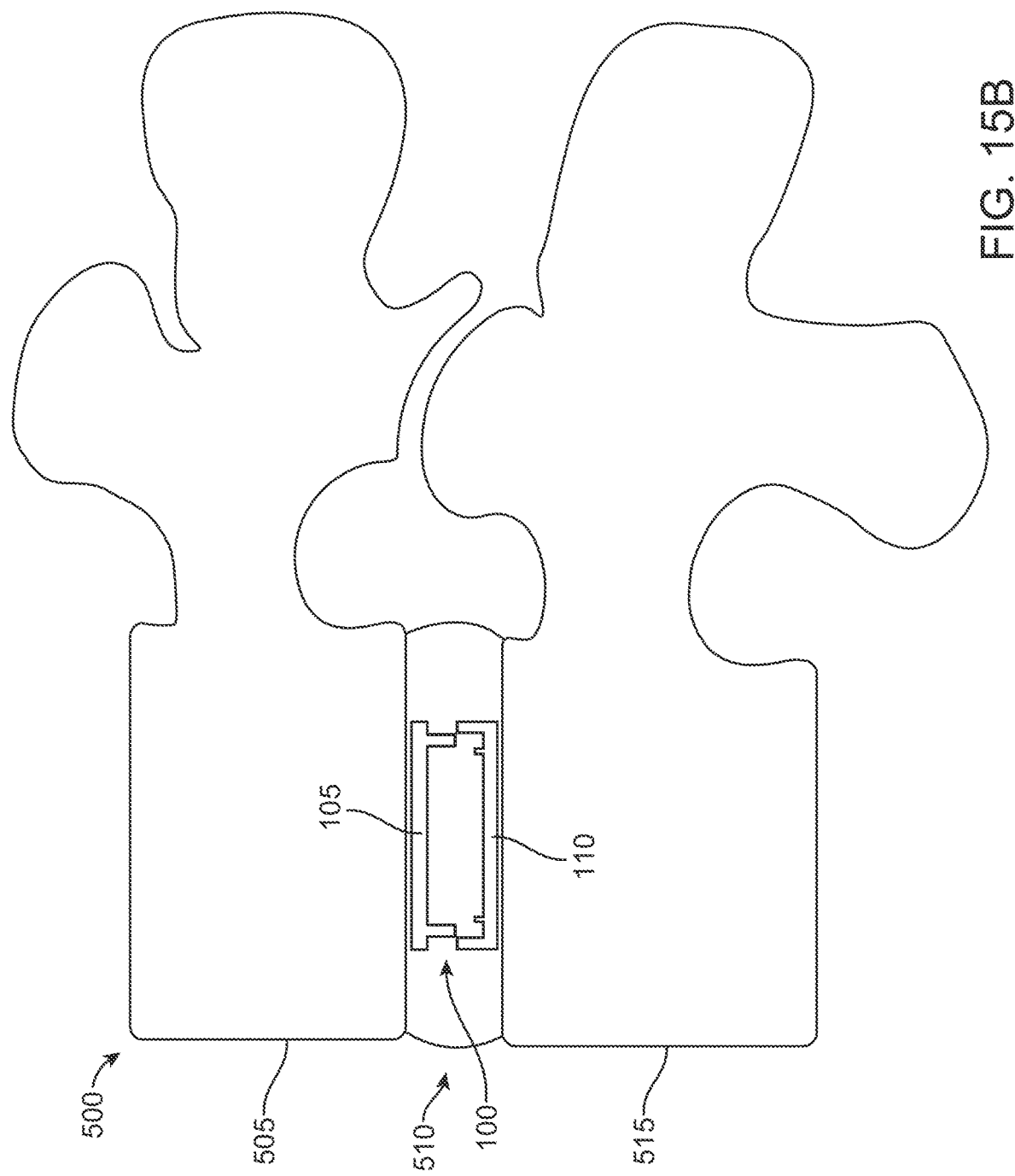

Turning now to FIG. 15B, a side or lateral view of the lumbar spine segment 500 is shown, in accordance with an illustrative embodiment. The lumbar spine segment 500 of FIG. 15B includes the cephalad vertebra 505, the caudal vertebra 515, and the intervertebral disk space 510. However, in contrast to the configuration of FIG. 15A, which depicted the expandable cage 100 in a contracted configuration, FIG. 15B depicts the expandable cage in an expanded configuration. The expansion of the expandable cage 100 increases the height of the intervertebral disk space 510, as the top portion 105 of the expandable cage is pushed against the cephalad vertebra 505 in a cephalad direction and the bottom portion 110 of the expandable cage is pushed against the caudal vertebra 515 in a caudal direction.

Figure 15C:
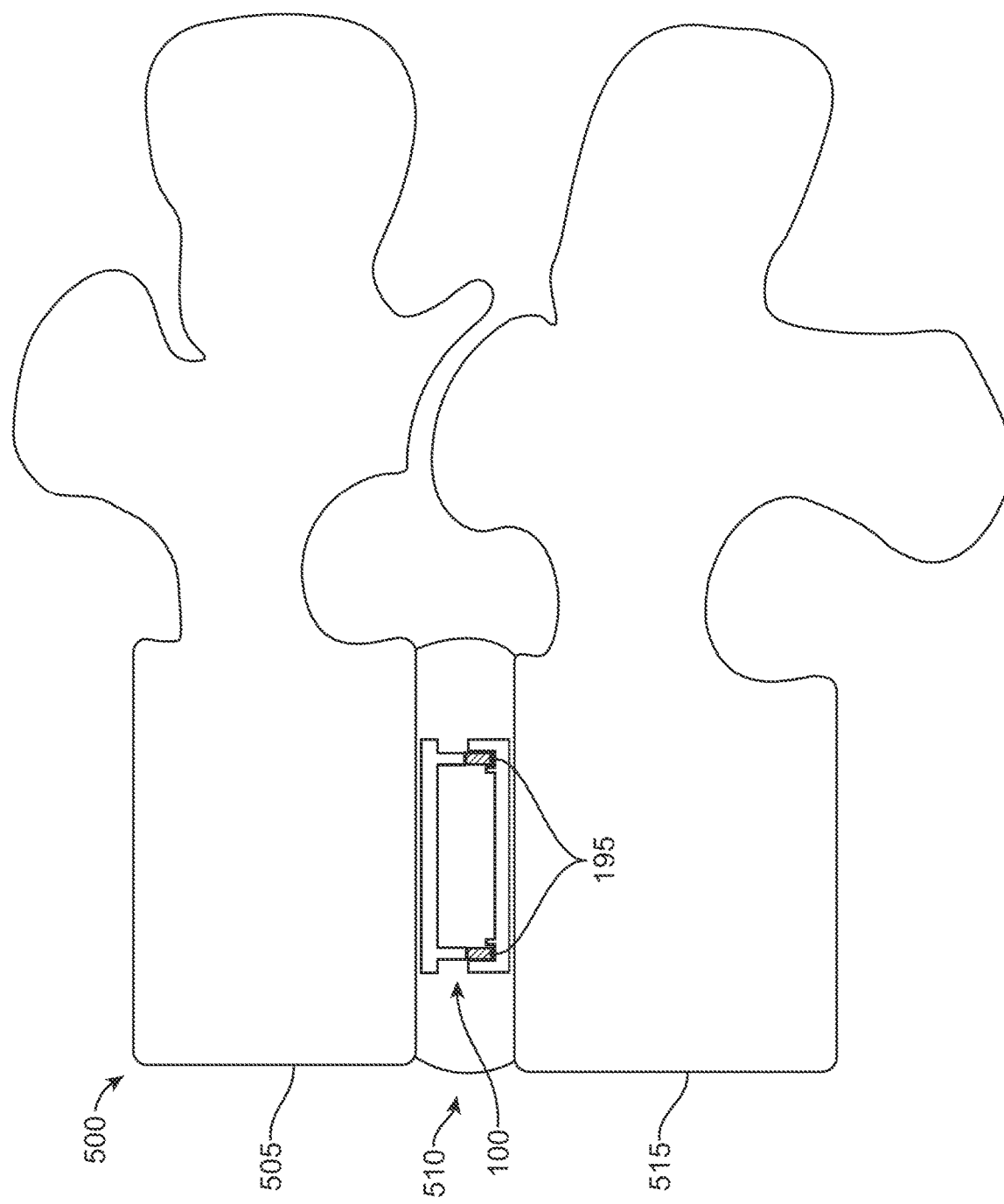

Referring now to FIG. 15C, the expandable cage 100 is shown in an expanded position as seen in FIG. 15B, now with the shims 195 inserted into the expandable cage and holding the expandable cage in an expanded position. The lumbar spine segment 500, as depicted, includes the cephalad vertebra 505, the caudal vertebra 515, and the intervertebral disk space 510. The shims 195 hold the expandable cage 100 in an expanded position, which results in an increase in the height of the intervertebral disk space 510.

Figure 16:
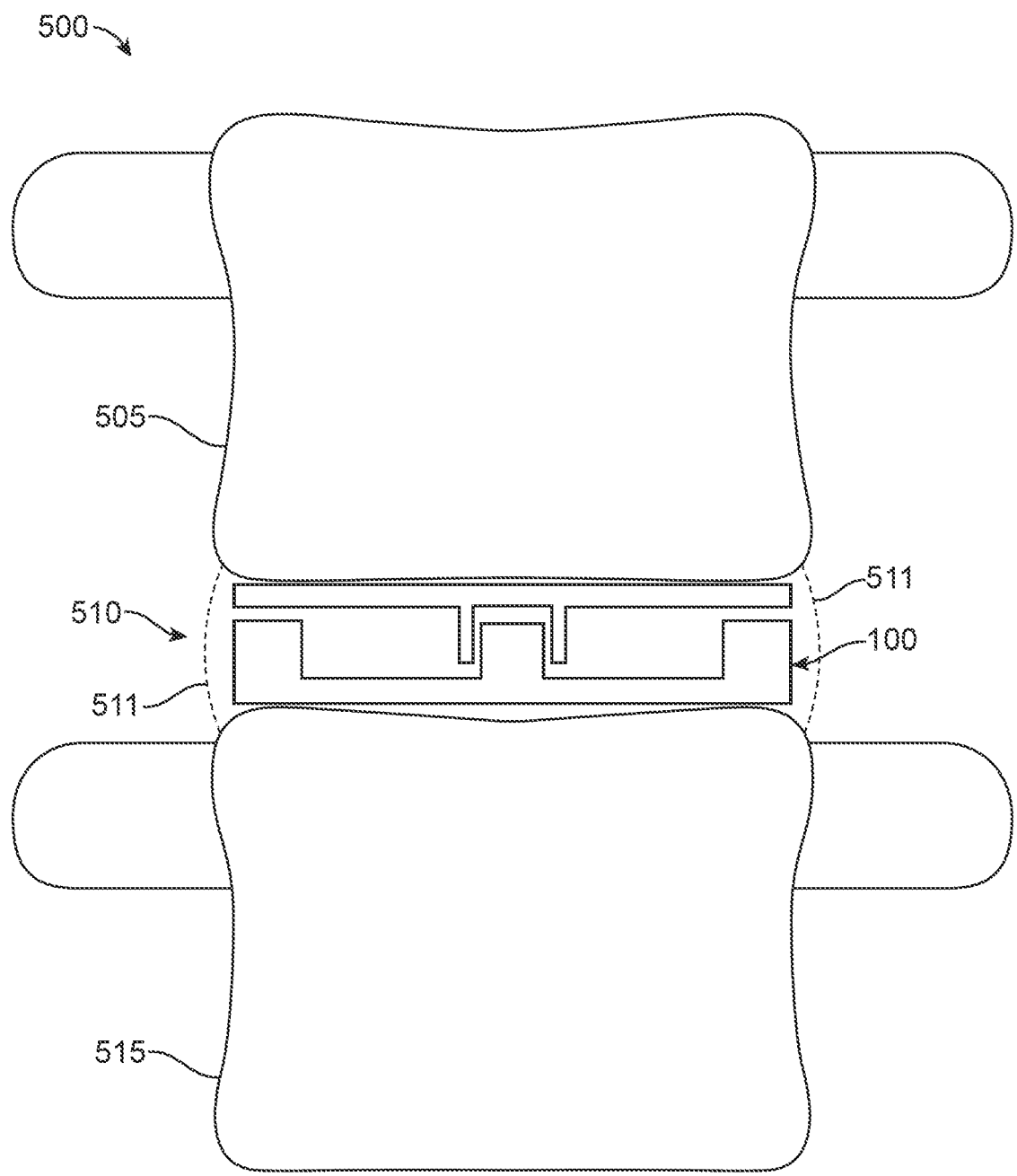
FIG. 16 is an anterior or front view of a portion of the lumbar spine with the expandable cage inserted and positioned in the interbody space, in accordance with an illustrative embodiment.

Turning now to FIG. 16, a front or anterior view of the lumbar spine segment 500 is shown, in accordance with an illustrative embodiment. The lumbar spine segment 500 includes the cephalad vertebra 505, the caudal vertebra 515, and the intervertebral disk space 510, as discussed above. A front or anterior view of the expandable cage 100 is depicted in the intervertebral disk space 510, after a diskectomy has been performed to sufficient extent that the expandable cage can be inserted into the intervertebral disk space. Disk annulus 511 is depicted having been partially or completely removed during the diskectomy process, prior to insertion of the expandable cage 100. The expandable cage 100 is depicted in a relatively contracted configuration, for example, in a similar configuration as shown in FIG. 15A. The expandable cage 100 may be expanded to the expanded configuration of FIGS. 15B-C. Further, as discussed above, the dimensions of the expandable cage 100 may be varied as desired based upon the size of the intervertebral disk space 510. For example, the expandable cage 100 may be longer or shorter in the medial-to-lateral dimension.

Figure 17:
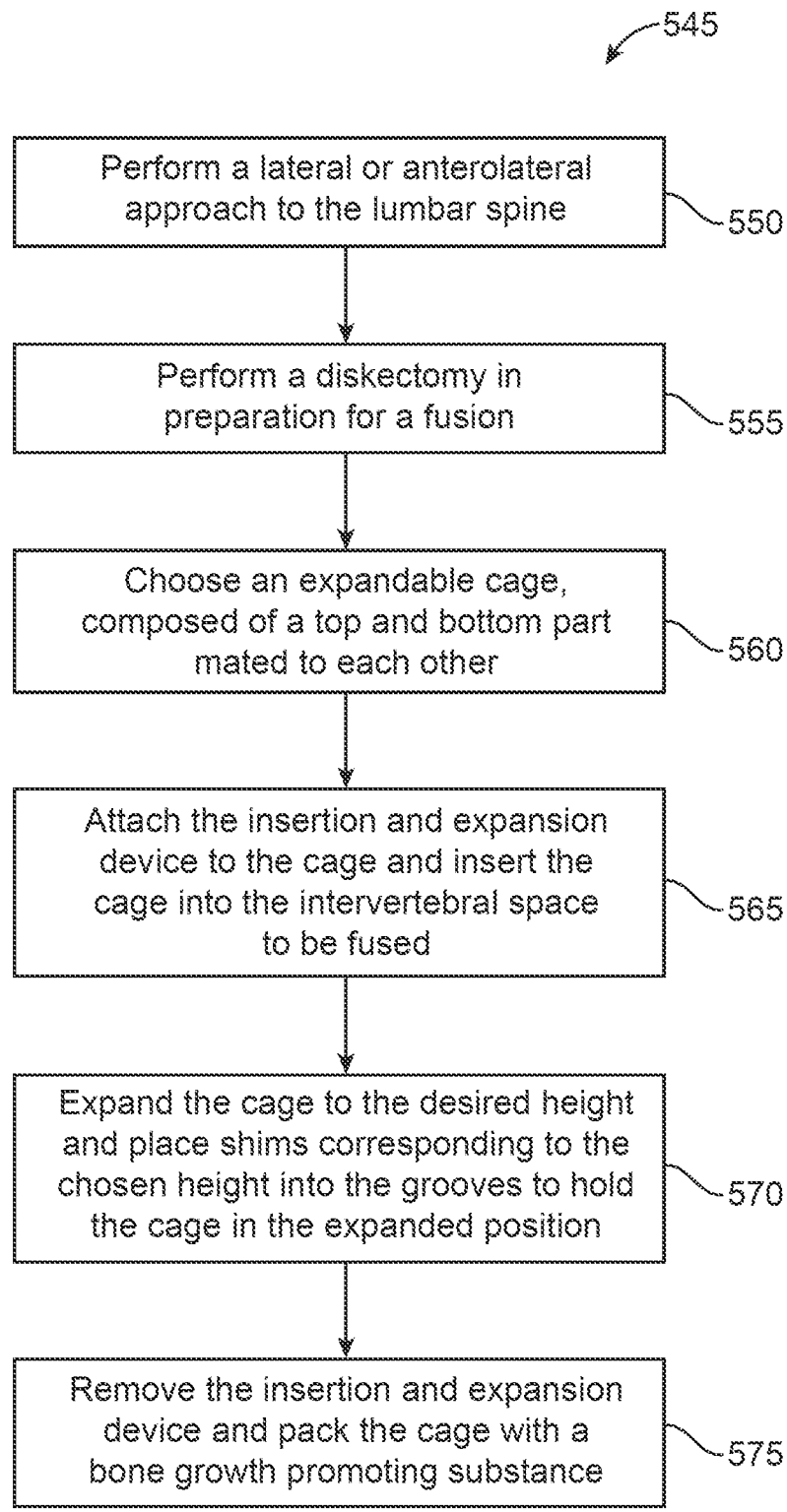
FIG. 17 is a flowchart outlining a process of using the expandable cage, in accordance with an illustrative embodiment.

Turning now to FIG. 17, a flow chart outlining a process 545 for performing a lumbar spine lateral fusion using a lateral extrinsically expandable cage (e.g., the expandable cage 100, 200, 285, and 310) is shown, in accordance with an illustrative embodiment. In alternative embodiments, fewer, additional, and/or different operations may be performed, including thoracic fusions. In an operation 550, a surgeon performs a lateral or anterolateral approach, or alternative approach, to the lumbar spine in a fashion known to those of skill in the art. In an operation 555, a diskectomy is performed in preparation for a fusion. In an operation 560, depending on the patient anatomy and the surgical approach, an expandable cage (e.g., the expandable cage 100, 200, 285, 310) is chosen to accommodate the anatomy. The top and bottom parts of the expandable cage (e.g., the expandable cage 100, 200, 285, 310) mate or engage with each other and may slide vertically, but are constrained in the anterior-posterior and medial-lateral planes, allowing for cage height expansion vertically within the limits of the cage component parameters. In an operation 565, the insertion and expansion device is attached to the expandable cage (e.g., the expandable cage 100, 200, 285, 310). The insertion and expansion device may rest between the top and bottom parts of the cage, or may be attached to the expandable cage via holes (e.g., the holes 315, 330) in the top and bottom portions of the cage, or a combination thereof. In the operation 565, the expandable cage is then inserted into the intervertebral disk space to be fused. In an operation 570, the expandable cage is expanded to the desired height with the insertion and expansion device, and shims corresponding to the selected height are slid into the grooves in the bottom portion of the expandable cage. The shims are configured to hold the expandable cage in an expanded position. In an operation 575, the insertion and expansion device is removed and the expandable cage is packed with bone growth promoting material such as bone graft and/or bone graft substitute, and the surgeon completes the fusion procedure in a manner known to those of skill in the art.

In an alternative embodiment, some or all of the bone growth promoting material may be placed in the expandable cage prior to insertion. In an alternative embodiment, the process 545 may be used for a thoracic or thoracolumbar or lumbosacral fusion using the expandable cage (e.g., the expandable cage 100, 200, 285, 310). Upon completion of the procedure, the surgical instruments and non-implanted components of the lateral extrinsically expandable cage are removed from the surgical site and the incision is closed.

Thus, the present disclosure provides an extrinsically expandable lumbar spine fusion cage that includes top and bottom portions that mate with each other, and are free to move with respect to each other in a cephalad-caudal (i.e., vertical) direction, thereby expanding or contracting an overall cage height. The top and bottom portions are constrained from moving with respect to each other in anterior-posterior and medial-lateral planes. Cage expansion occurs via an insertion and expansion device that is not part of the cage itself, but attaches to the cage. The cage is inserted into the intervertebral disk space to be fused after a diskectomy is performed. After insertion, the cage is expanded to a desired height. Once the cage is expanded and the top and bottom portions of the cage are pressed firmly against the adjacent vertebral endplates by virtue of the presence of the cage within the disk space, the cage is held in the expanded position by arms that extend outwardly from the top and bottom portions. The top arms rest on shims that are inserted into grooves in the bottom portion of the cage, the shims in turn resting on a lower section of the bottom portion of the cage. Once the insertion and expansion device is removed, the top and bottom portions of the cage are held in the expanded position by the shims, and collectively the top and bottom parts of the cage and the shims comprise the lateral extrinsically expandable cage. Shims may be made in different sizes in order to hold the cage in various expanded heights and configurations. Once the shims are inserted and the insertion and expansion device removed, a bone growth promoting substance such as bone graft and/or bone graft substitute may be placed within the cage to provide the biological component of the fusion operation. Thus, the cage provides structural support to the spine between adjacent vertebral bodies to be fused.

In some embodiments, the shims may be contained within grooves in the top or bottom portions of the cage, or in some embodiments the shims may not be contained within grooves. In some embodiments, the cage may be designed to accommodate shims of different heights, such as with an anterior shim taller than a posterior shim, or a posterior shim taller than an anterior shim, thus allowing for in-situ modulation of the sagittal cage configuration, which in turn affects the degree of lordosis or kyphosis across the spinal segment that is receiving the cage. In some embodiments, a bone growth promoting substance such as bone graft or bone graft substitute may then be packed into the cage.

Thus, the present disclosure provides an extrinsically expandable cage, which is configured to be expanded using a removable insertion and expansion device from outside of the spinal cavity. The insertion and expansion device is not configured to be part of the expandable cage after the insertion of the shims into the expandable cage. By virtue of expanding the expandable cage using an extrinsic mechanism that does not form a part of the final expandable cage, the present disclosure provides an expandable cage that may achieve greater height expansion and contraction compared to conventional expandable cages. Further, by removing the insertion and expansion device from the expandable cage, the insertion and expansion devices does not take up any unnecessary space within the expandable cage, which may then be used to fill in additional bone graft promoting material. The cost and complexity of the expandable cage is also reduced.

In some embodiments, part of the expandable cage design may include an expansion limiter such that the expandable cage may not be over-expanded, which may result in disengagement of the top portion of the expandable cage from the bottom portion of the expandable cage. In some embodiments, the lateral extrinsically expandable cage may include blocking mechanisms to ensure the shims remain confined within the expandable cage. In some embodiments, part of the expandable cage design may also include an optional device that may be inserted and attached onto a lateral wall of the expandable cage opposite the insertion device to prevent the bone growth promoting substance from extruding through the opening of the expandable cage that is opposite the insertion and expansion device. In some embodiments, a cage insertion device may be separate from a cage expansion device. An insertion and expansion device may be used that rests in part between the top and bottom portions of the expandable cage, or that attaches to a lateral aspect of the expandable cage, and is used to insert the expandable cage into the intervertebral space to be fused and then extrinsically expand the expandable cage to the desired height, and later removed in their entirety after shim placement.

The components (e.g., the top portion, bottom portion, shims) described herein may be made in a variety of lengths and/or shapes to accommodate various patient anatomies and surgeon preferences. The components can be made from a variety of biologically compatible materials suitable for medical applications, including but not limited to metals, bone material, ceramics, and synthetic composites. For example, the components of a lateral extrinsically expandable cage may be fabricated from materials such as titanium, titanium alloys, cobalt-chrome alloys, stainless steel, stainless steel alloys, thermoplastics such as polyether ether ketone (PEEK) and other similar substances, carbon fiber, carbon fiber composites, ceramics and composites, aluminum, allograft bone, xenograft bone, any combination of the above substances, or any suitable material that is able to withstand the biomechanical stresses under which they are placed.

The exemplary embodiments of the surgical system and related methods are discussed in terms of medical devices used for the treatment of spinal disorders. In some embodiments, the systems and methods of the present disclosure are employed with a spinal fusion, for example, with a thoracic, lumbar and/or sacral region of the spine.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the disclosure be defined by the claims appended hereto and their equivalents.

What is claimed is:

1. A method comprising:
    inserting an expandable cage within a spinal cavity;
    expanding the expandable cage to an expanded position within the spinal cavity, wherein the expanding comprises moving a top portion of the expandable cage away from a bottom portion of the expandable cage using an expansion device;
    inserting a first shim and a second shim within the expandable cage and between the top portion and the bottom portion for holding the expandable cage in the expanded position;
    removing the expansion device; and
    attaching the expansion device to the expandable cage before inserting the expandable cage within the spinal cavity by:
        engaging the expansion device with holes on a sidewall of the top portion of the expandable cage; and
        engaging the expansion device with corresponding holes on a sidewall of the bottom portion of the expandable cage.

2. The method of claim 1, further comprising packing an opening of the expandable cage with a bone graft promoting material for facilitating contact of the bone graft promoting material with an adjacent vertebral endplate.

3. The method of claim 1, further comprising using the expansion device as an insertion device for positioning the expandable cage between adjacent vertebral endplates within the spinal cavity.

4. The method of claim 1, further comprising expanding the expandable cage in either a lordotic or a kyphotic configuration within the spinal cavity.

5. The method of claim 1, wherein the top portion comprises an outwardly extending top arm and the bottom portion comprises an outwardly extending bottom arm.

6. The method of claim 5, further comprising:
    engaging the bottom arm with the top arm, wherein upon engagement, the top portion and the bottom portion are substantially restricted from movement relative to each other in an anterior-posterior direction and in a medial-lateral direction.

7. The method of claim 1, further comprising:
    adjusting a height of the expandable cage using the expansion device.

8. The method of claim 1, wherein removing the expansion device comprises removing one or more fasteners that secure the expansion device to the expandable cage.

9. The method of claim 1, wherein the expansion device comprises:
    an upper handle having a first upper end and a second upper end, wherein the first upper end is configured to connect to an upper extension;
    a lower handle having a first lower end and second lower end, wherein the first lower end is configured to connect to a lower extension;
    a middle joint located a first distance from the first lower end and a second distance from the first upper end, wherein the upper handle is configured to articulate relative to the lower handle at the middle joint via a hinge;
    the upper extension having a first upper portion and a second upper portion, wherein the first upper portion is configured to connect to the first upper end of the upper handle via an upper joint, and wherein the upper extension is configured to articulate relative to the upper handle at the upper joint; and
    the lower extension having a first lower portion and a second lower portion, wherein the first lower portion is configured to connect to the first lower end of the lower handle via a lower joint, and wherein the lower extension is configured to articulate relative to the lower handle at the lower joint.

10. The method of claim 9, wherein expanding the expandable cage using the expandable device comprises pressing the upper extension against the top portion and pressing the lower extension against the bottom portion.

11. A method, comprising:
    inserting an expandable cage in a contracted position within a spinal cavity, wherein the expandable cage includes a top portion engaged with a bottom portion;

positioning the expandable cage between a first vertebra and a second vertebra;

expanding the top portion relative to the bottom portion for obtaining an expanded position for facilitating fusion of the first vertebra and the second vertebra;

inserting a shim between the top portion and the bottom portion for holding the expandable cage in the expanded position; and attaching an expansion device to the expandable cage before inserting the expandable cage within the spinal cavity by:
- engaging the expansion device with holes on a sidewall of the top portion of the expandable cage; and
- engaging the expansion device with corresponding holes on a sidewall of the bottom portion of the expandable cage.

12. The method of claim 11, further comprising adjusting a height of the expandable cage in a cephalad-caudal direction by replacing the shim with another shim corresponding to the height of the expandable cage.

13. The method of claim 11, further comprising:
- sliding the shim via an opening of a groove provided on the bottom portion of the expandable cage;
- sliding the shim within the groove until the shim hits an end projection provided at an end opposite the opening of the groove; and
- restricting motion of the shim within the groove by engaging a lip of a top arm of the top portion with the shim on a side facing the opening.

14. The method of claim 13, wherein the top arm extends outwardly from the top portion, wherein the bottom portion comprises an outwardly extending bottom arm.

15. The method of claim 14, wherein the top arm includes a first set of top arms and a second set of top arms, and wherein the bottom arm includes:
- a first set of bottom arms configured to engage with the first set of top arms, and
- a second set of bottom arms configured to engage with the second set of top arms.

16. The method of claim 15, wherein the top portion has a first outward facing side and the bottom portion has a second outward facing side, each of the first outward facing side and the second outward facing side comprising a first set of one or more holes, each of the one or more holes configured to receive a fastener.

17. The method of claim 11, wherein, in the expanded position, motion of the top portion relative to the bottom portion in an anterior-posterior direction and in a medial-lateral direction is substantially restricted.

18. The method of claim 11, further comprising packing an opening of the expandable cage with a bone graft promoting material for facilitating contact of the bone graft promoting material with an adjacent vertebral endplate.

19. The method of claim 18, wherein the opening is disposed within at least one of the top portion or the bottom portion.

\* \* \* \* \*